(12) United States Patent
Ito et al.

(10) Patent No.: US 8,795,516 B2
(45) Date of Patent: Aug. 5, 2014

(54) GYPSUM DEWATERING DEVICE FOR DESULFURIZATION FACILITY

(75) Inventors: Hideki Ito, Tokyo (JP); Naoyuki Kamiyama, Tokyo (JP); Makoto Tsutsui, Tokyo (JP); Seiji Kagawa, Tokyo (JP); Tatsuto Nagayasu, Tokyo (JP); Norikazu Inaba, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 201 days.

(21) Appl. No.: 13/522,133

(22) PCT Filed: Sep. 30, 2010

(86) PCT No.: PCT/JP2010/067172
§ 371 (c)(1),
(2), (4) Date: Jul. 13, 2012

(87) PCT Pub. No.: WO2011/104919
PCT Pub. Date: Sep. 1, 2011

(65) Prior Publication Data
US 2012/0285326 A1    Nov. 15, 2012

(30) Foreign Application Priority Data
Feb. 26, 2010 (JP) .................. 2010-042051

(51) Int. Cl.
*B01D 53/50* (2006.01)
*B01D 33/04* (2006.01)
*C01F 11/46* (2006.01)
*C02F 103/18* (2006.01)

(52) U.S. Cl.
CPC ............ *B01D 53/501* (2013.01); *B01D 53/504* (2013.01); *B01D 2251/404* (2013.01); *B01D 2251/606* (2013.01); *B01D 2258/0283* (2013.01); *B01D 33/04* (2013.01); *B01D 2201/204* (2013.01); *C01F 11/464* (2013.01); *C02F 2103/18* (2013.01)
USPC ........... 210/103; 210/184; 210/400; 210/406; 96/241; 96/242; 96/244; 96/253

(58) Field of Classification Search
CPC .... B01D 53/50; B01D 53/501; B01D 53/504; B01D 53/75; B01D 2251/404; B01D 2251/606; B01D 2258/0283; B01D 2033/044; B01D 2033/048; B01D 2033/2201; B01D 2033/204; B01D 33/04; C01F 11/464; C02F 11/123; C02F 2103/18
USPC .............. 96/240, 241, 242, 244, 253; 95/205, 95/235; 210/103, 184, 400, 401, 406; 422/168
See application file for complete search history.

(56) References Cited

U.S. PATENT DOCUMENTS

| | | | | |
|---|---|---|---|---|
| 4,341,628 A | * | 7/1982 | Fujinami et al. | 210/101 |
| 5,133,872 A | * | 7/1992 | Baldwin et al. | 210/709 |
| 5,635,074 A | * | 6/1997 | Stenstrom et al. | 210/739 |
| 5,648,048 A | * | 7/1997 | Kuroda et al. | 422/168 |
| 5,902,555 A | * | 5/1999 | Tatani et al. | 422/168 |

FOREIGN PATENT DOCUMENTS

| | | |
|---|---|---|
| JP | 09-024203 A | 1/1997 |
| JP | 11-128670 A | 5/1999 |
| JP | 11-151419 A | 6/1999 |
| JP | 2000-061257 A | 2/2000 |
| JP | 2002-186805 A | 7/2002 |
| JP | 2002-233730 A | 8/2002 |
| JP | 2006-110426 A | 4/2006 |

OTHER PUBLICATIONS

Notice of Allowance dated Jun. 11, 2013, issued in corresponding Japanese application No. 2010-042051, with English Translation.
International Search Report of PCT/JP2010/067172, mailing date Nov. 16, 2010.
Japanese Written Opinion of PCT/JP2010/067172, mailing date Nov. 16, 2010.

Translation of Japanese Written Opinion of PCT/JP2010/067172, mailing date Nov. 16, 2010, which was previously submitted on Jul. 13, 2012.

* cited by examiner

*Primary Examiner* — Frank Lawrence, Jr.
(74) *Attorney, Agent, or Firm* — Westerman, Hattori, Daniels & Adrian, LLP

(57) ABSTRACT

A gypsum dewatering device 2 installed in a desulfurization facility 105 in which sulfur oxide in flue gas G is absorbed by limestone in an absorber 1, includes a belt filter 22 that absorbs sulfur oxide and dewaters gypsum slurry SS fed from the absorber 1 to form a gypsum cake SC, a vacuum suction mechanism 23 that sucks moisture in the gypsum cake SC via the belt filter 22, a moisture measuring means H1 that measures a moisture content of the gypsum cake SC to be dewatered by the belt filter 22, a heating means 25 that heats the gypsum cake SC dewatered by the belt filter 22 by hot water or steam, and a control means 26 that controls a heated state by the heating means 25 when the moisture content of the gypsum cake SC input from the moisture measuring means H1 has exceeded a predetermined amount.

21 Claims, 9 Drawing Sheets

GYPSUM DEWATERING DEVICE FOR DESULFURIZATION FACILITY

FIELD

The present invention relates to a gypsum dewatering device that performs dewatering of a gypsum cake in a desulfurization facility using a limestone-gypsum method.

BACKGROUND

In a desulfurization facility in which $SO_2$ in flue gas is desulfurized by a limestone-gypsum method, a gypsum dewatering device that acquires gypsum by dewatering gypsum slurry generated in a desulfurization process is applied. As a type of the gypsum dewatering device, there is a gypsum dewatering device that uses a belt filter, in which a filter fabric is arranged in a belt-like shape, and a vacuum pump and a decompression mechanism are provided below the belt, to dewater gypsum slurry fed onto the belt by vacuum suction from below the belt, while advancing the filter fabric belt in a horizontal direction. However, the gypsum slurry contains fine impurities, for example, fine particle dust including silica ($SiO_2$), aluminum oxide ($AlO_3$), and unburned carbon. Therefore, if a fine particle dust layer is formed on the uppermost layer on the surface of a gypsum cake on the belt filter, which is formed in a uniform thickness, while dewatering the gypsum slurry, the air permeability is deteriorated at the time of vacuum suction, thereby causing a decrease in the dewatering performance. When the dewatering performance decreases, the adhesive property of the gypsum cake increases, and this causes a problem such that the gypsum cake adheres to the circumference in a transportation process. Consequently, the quality of the gypsum does not meet a criteria (for example, 10 wt %), and the gypsum cannot be sold as a product, and thus the disposal cost for disposing it as industrial waste is required.

Conventionally, therefore, for example, in a belt filter described in Patent Literature 1, comb-like gates are provided in a plurality of stages in a longitudinal direction of the belt filter, whose lower ends extend to an upper layer of a gypsum cake, so that a fine particle layer formed on the surface of the gypsum cake is stirred, thereby improving its dewaterability.

CITATION LIST

Patent Literature

Patent Literature 1: Japanese Patent Application Laid-open No. 11-128670

SUMMARY

Technical Problem

However, in the belt filter described in Patent Literature 1, when impurities and a salt concentration in the gypsum slurry become excessive, the gypsum slurry flows into a portion stirred by the gates, inhibiting the improvement of the dewaterability again, and thus expected effects may not be acquired.

The present invention has been achieved to solve the above problems, and an object of the present invention is to provide a gypsum dewatering device for a desulfurization facility that can maintain the dewatering performance.

Solution to Problem

According to an aspect of the present invention, a gypsum dewatering device for a desulfurization facility that is installed in a desulfurization facility in which sulfur oxide in flue gas is absorbed by limestone in an absorbent in an absorber, include: a belt filter that absorbs the sulfur oxide and dewaters gypsum slurry fed from the absorber to form a gypsum cake; a vacuum suction mechanism that sucks moisture in the gypsum cake via the belt filter; a moisture measuring unit that measures a moisture content of the gypsum cake to be dewatered by the belt filter; a heating unit that heats the gypsum cake to be dewatered by the belt filter by hot water or steam; and a control unit that controls a heated state by the heating unit, when a moisture content of the gypsum cake input from the moisture measuring unit has exceeded a predetermined amount.

According to the gypsum dewatering device for a desulfurization facility, the moisture content in the dewatered gypsum cake in the belt filter is measured by the moisture measuring unit and monitored at all times, thereby quickly ascertaining insufficient dewatering and promptly restoring the insufficient dewatering. Accordingly, the dewatering performance for dewatering the gypsum cake can be maintained.

Advantageously, in the gypsum dewatering device for a desulfurization facility, further includes a suction-pressure measuring unit that measures a suction pressure by the vacuum suction mechanism, and when the moisture content of the gypsum cake input from the moisture measuring unit has exceeded a predetermined amount and an input value from the suction-pressure measuring unit has deviated from a predetermined set value, the control unit controls a heated state by the heating unit.

According to the gypsum dewatering device for a desulfurization facility, the dewatering performance for dewatering the gypsum cake can be maintained, and an initial indication of a decrease in the dewatering performance can be ascertained by an input value from the suction-pressure measuring unit.

Advantageously, in the gypsum dewatering device for a desulfurization facility, further includes an impurity salt concentration measuring unit that measures a salt concentration as impurities in the absorber, wherein when the moisture content of the gypsum cake input from the moisture measuring unit has exceeded a predetermined amount and an input from the impurity salt concentration measuring unit has deviated from a predetermined set value, the control unit controls a heated state by the heating unit.

According to the gypsum dewatering device for a desulfurization facility, the dewatering performance for dewatering the gypsum cake can be maintained, and an initial indication of a decrease in the dewatering performance can be ascertained by an input value from the impurity salt concentration measuring unit.

Advantageously, in the gypsum dewatering device for a desulfurization facility, further includes a specific resistance-to-filtration measuring unit that measures a specific resistance to filtration of the gypsum cake, and when the moisture content of the gypsum cake input from the moisture measuring unit has exceeded a predetermined amount and an input value from the specific resistance-to-filtration measuring unit has deviated from a predetermined set value, the control unit controls a heated state by the heating unit.

According to the gypsum dewatering device for a desulfurization facility, the dewatering performance for dewatering the gypsum cake can be maintained, and an initial indication of a decrease in the dewatering performance can be ascertained by an input value from the specific resistance-to-filtration measuring unit.

Advantageously, in the gypsum dewatering device for a desulfurization facility, further includes: a suction-pressure measuring unit that measures a suction pressure by the vacuum suction mechanism; and an impurity salt concentration measuring unit that measures a salt concentration as impurities in the absorber. When the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls a heated state by the heating unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit and the impurity salt concentration measuring unit.

Advantageously, in the gypsum dewatering device for a desulfurization facility, further includes: a suction-pressure measuring unit that measures a suction pressure by the vacuum suction mechanism; an impurity salt concentration measuring unit that measures a salt concentration as impurities in the absorber; and a specific resistance-to-filtration measuring unit that measures a specific resistance to filtration of the gypsum cake. When the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls a heated state by the heating unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit, the impurity salt concentration measuring unit, and the specific resistance-to-filtration measuring unit.

According to another aspect of the present invention, a gypsum dewatering device for a desulfurization facility that is installed in a desulfurization facility in which sulfur oxide in flue gas is absorbed by limestone in an absorbent in an absorber, includes: a belt filter that absorbs the sulfur oxide and dewaters gypsum slurry fed from the absorber to form a gypsum cake; a vacuum suction mechanism that sucks moisture in the gypsum cake via the belt filter; a moisture measuring unit that measures a moisture content of the gypsum cake to be dewatered by the belt filter; a speed varying unit that varies a belt advancing rate by the belt filter; and a control unit that controls a belt advancing rate by the speed varying unit, when a moisture content of the gypsum cake input from the moisture measuring unit has exceeded a predetermined amount.

According to the gypsum dewatering device for a desulfurization facility, the moisture content in the dewatered gypsum cake in the belt filter is measured by the moisture measuring unit and monitored at all times, thereby quickly ascertaining insufficient dewatering and promptly restoring the insufficient dewatering. Accordingly, the dewatering performance for dewatering the gypsum cake can be maintained.

Advantageously, in the gypsum dewatering device for a desulfurization facility, further includes a suction-pressure measuring unit that measures a suction pressure by the vacuum suction mechanism, and when the moisture content of the gypsum cake input from the moisture measuring unit has exceeded a predetermined amount and an input value from the suction-pressure measuring unit has deviated from a predetermined set value, the control unit controls a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the suction-pressure measuring unit.

Advantageously, in the gypsum dewatering device for a desulfurization facility, further includes an impurity salt concentration measuring unit that measures a salt concentration as impurities in the absorber, and when the moisture content of the gypsum cake input from the moisture measuring unit has exceeded a predetermined amount and an input value from the impurity salt concentration measuring unit has deviated from a predetermined set value, the control unit controls a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the impurity salt concentration measuring unit.

Advantageously, in the gypsum dewatering device for a desulfurization facility, further includes a specific resistance-to-filtration measuring unit that measures a specific resistance to filtration of the gypsum cake, and when the moisture content of the gypsum cake input from the moisture measuring unit has exceeded a predetermined amount and an input value from the specific resistance-to-filtration measuring unit has deviated from a predetermined set value, the control unit controls a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the specific resistance-to-filtration measuring unit.

Advantageously, in the gypsum dewatering device for a desulfurization facility, further includes: a suction-pressure measuring unit that measures a suction pressure by the vacuum suction mechanism; and an impurity salt concentration measuring unit that measures a salt concentration as impurities in the absorber. When the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit and the impurity salt concentration measuring unit.

Advantageously, in the gypsum dewatering device for a desulfurization facility, further includes: a suction-pressure measuring unit that measures a suction pressure by the vacuum suction mechanism; an impurity salt concentration measuring unit that measures a salt concentration as impurities in the absorber, and a specific resistance-to-filtration measuring unit that measures a specific resistance to filtration of the gypsum cake. When the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit, the impurity salt concentration measuring unit, and the specific resistance-to-filtration measuring unit.

According to still another aspect of the present invention, a gypsum dewatering device for a desulfurization facility that is installed in a desulfurization facility in which sulfur oxide in flue gas is absorbed by limestone in an absorbent in an absorber, includes: a belt filter that absorbs the sulfur oxide and dewaters gypsum slurry fed from the absorber to form a gypsum cake; a vacuum suction mechanism that sucks moisture in the gypsum cake via the belt filter; a moisture measuring unit that measures a moisture content of the gypsum cake to be dewatered by the belt filter; a heating unit that heats the gypsum cake to be dewatered by the belt filter by hot water or steam; a speed varying unit that varies a belt advancing rate by the belt filter; and a control unit that controls both a heated state by the heating unit and a belt advancing rate by the speed varying unit, when a moisture content of the gypsum cake input from the moisture measuring unit has exceeded a predetermined amount.

According to the gypsum dewatering device for a desulfurization facility, the moisture content in the dewatered gypsum cake in the belt filter is measured by the moisture measuring unit and monitored at all times, thereby quickly ascertaining insufficient dewatering and promptly restoring the insufficient dewatering. Accordingly, the dewatering performance for dewatering the gypsum cake can be maintained.

Advantageously, in the gypsum dewatering device for a desulfurization facility, further includes a suction-pressure measuring unit that measures a suction pressure by the vacuum suction mechanism, and when the moisture content of the gypsum cake input from the moisture measuring unit has exceeded a predetermined amount and an input value from the suction-pressure measuring unit has deviated from a predetermined set value, the control unit controls both a heated state by the heating unit and a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the suction-pressure measuring unit.

Advantageously, in the gypsum dewatering device for a desulfurization facility, further includes an impurity salt concentration measuring unit that measures a salt concentration as impurities in the absorber, and when the moisture content of the gypsum cake input from the moisture measuring unit has exceeded a predetermined amount and an input value from the impurity salt concentration measuring unit has deviated from a predetermined set value, the control unit controls both a heated state by the heating unit and a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the impurity salt concentration measuring unit.

Advantageously, in the gypsum dewatering device for a desulfurization facility, further includes a specific resistance-to-filtration measuring unit that measures a specific resistance to filtration of the gypsum cake, and when the moisture content of the gypsum cake input from the moisture measuring unit has exceeded a predetermined amount and an input value from the specific resistance-to-filtration measuring unit has deviated from a predetermined set value, the control unit controls both a heated state by the heating unit and a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from the specific resistance-to-filtration measuring unit.

Advantageously, in the gypsum dewatering device for a desulfurization facility, further includes: a suction-pressure measuring unit that measures a suction pressure by the vacuum suction mechanism; and an impurity salt concentration measuring unit that measures a salt concentration as impurities in the absorber. When the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls both a heated state by the heating unit and a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit and the impurity salt concentration measuring unit.

Advantageously, in the gypsum dewatering device for a desulfurization facility, further includes: a suction-pressure measuring unit that measures a suction pressure by the vacuum suction mechanism; an impurity salt concentration measuring unit that measures a salt concentration as impurities in the absorber; and a specific resistance-to-filtration measuring unit that measures a specific resistance to filtration of the gypsum cake. When the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls both a heated state by the heating unit and a belt advancing rate by the speed varying unit.

According to the gypsum dewatering device for a desulfurization facility, the dewatering performance for dewatering the gypsum cake can be maintained, and an initial indication of a decrease in the dewatering performance can be ascertained by an input value from at least one of the suction-pressure measuring unit, the impurity salt concentration measuring unit, and the specific resistance-to-filtration measuring unit.

Advantageously, in the gypsum dewatering device for a desulfurization facility, further includes a surface-temperature measuring unit that measures a surface temperature of the gypsum cake, and when a surface temperature input from the surface-temperature measuring unit is not equal to or lower than a predetermined value, the control unit controls to decrease heating by the heating unit.

According to the gypsum dewatering device for a desulfurization facility, the surface temperature of the gypsum cake is maintained to be equal to or lower than a predetermined value. Accordingly, excessive moisture due to condensation of steam is prevented, thereby avoiding a state such that moisture in the gypsum cake increases.

Advantageously, in the gypsum dewatering device for a desulfurization facility, further includes: a desulfurization-amount measuring unit that measures an absorption amount of the sulfur oxide in the absorber; a transporting-rate varying unit that varies a transporting rate of the gypsum cake to be dewatered by the belt filter; and a speed varying unit that varies a belt advancing rate of the belt filter. When a moisture content of the gypsum cake input from the moisture measuring unit has exceeded a predetermined amount, if each input value of the suction-pressure measuring unit, the impurity salt concentration measuring unit, and the specific resistance-to-filtration measuring unit does not deviate from a predetermined set value, the control unit controls both an increase in the transporting rate of the transporting-rate varying unit and the belt advancing rate of the speed varying unit, when the absorption amount input from the desulfurization-amount measuring unit has exceeded a predetermined amount.

According to the gypsum dewatering device for a desulfurization facility, the dewatering performance for dewatering the gypsum cake can be maintained. Furthermore, even when it is difficult to ascertain an initial indication of a decrease in the dewatering performance by an input value from at least one of the suction-pressure measuring unit, the impurity salt concentration measuring unit, and the specific resistance-to-filtration measuring unit, an initial indication of a decrease in the dewatering performance can be ascertained by an input value from the desulfurization-amount measuring unit.

Advantageous Effects of Invention

According to the present invention, by eliminating a dewatering-performance degrading factor in advance, the dewatering performance can be maintained.

DESCRIPTION OF EMBODIMENTS

Exemplary embodiments of the present invention will be explained below in detail with reference to the accompanying drawings. The present invention is not limited to the embodiments. In addition, constituent elements in the following embodiments include those that can be easily replaced by persons skilled in the art, or that are substantially equivalent.

First Embodiment

Figure 1:
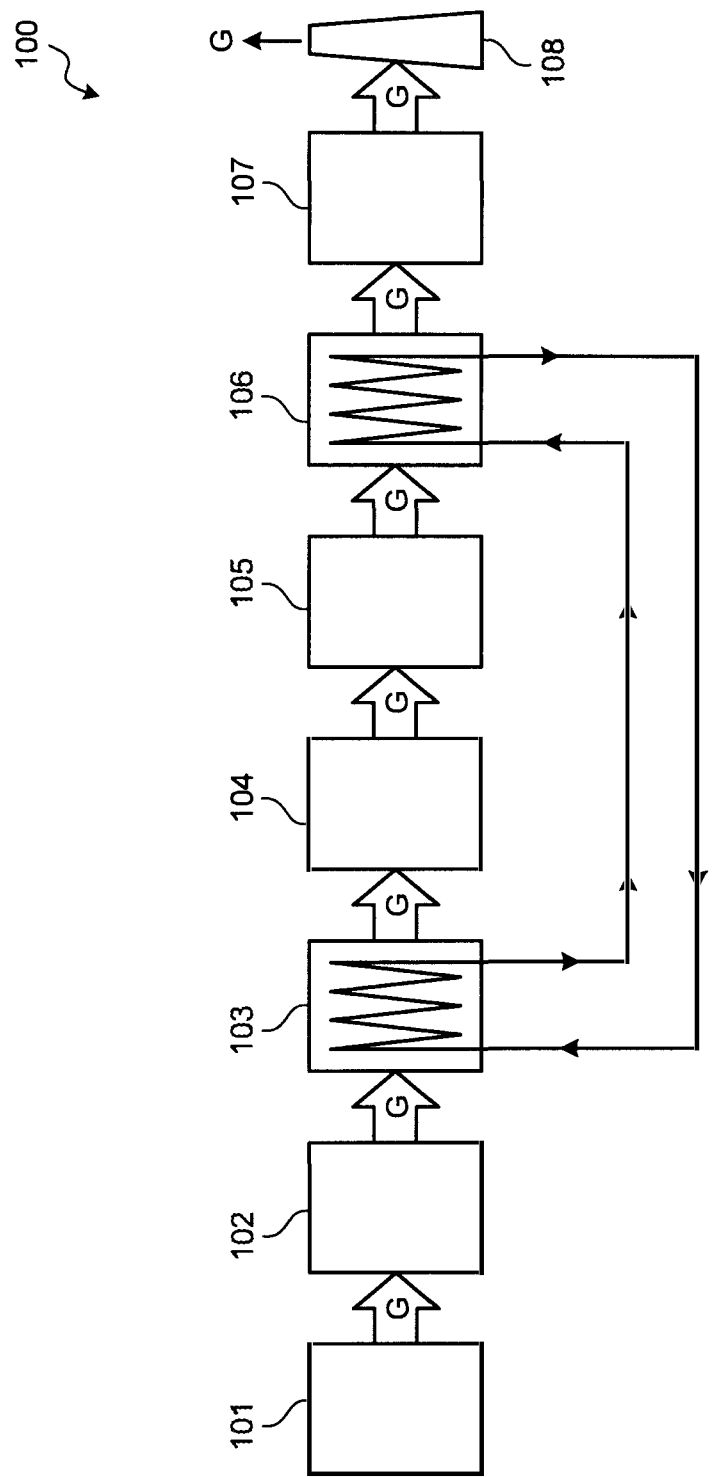
FIG. 1 is a schematic diagram of an air pollution control system to which a desulfurization facility is applied.

A first embodiment of the present invention is explained with reference to the drawings. FIG. 1 is a schematic diagram of an air pollution control system to which a desulfurization facility according to the present embodiment is applied.

As shown in FIG. 1, an air pollution control system 100 removes nitrogen oxide ($NO_x$), dust, sulfur oxide ($SO_x$), and carbon dioxide ($CO_2$) contained in flue gas G in a process in which the flue gas G discharged from a boiler 101 in a power generation plant, a factory or the like is emitted from a stack 108.

The flue gas G discharged from the boiler 101 is introduced into a desulfurization facility 102 filled with a catalyst. In the desulfurization facility 102, nitrogen oxide contained in the flue gas G is reduced to water and nitrogen and rendered harmless by ammonia ($NH_3$) injected as a reducing agent.

The flue gas G having passed through the desulfurization facility 102 is introduced into a heat recovery facility 103, which is a heat exchanger of a gas heater, and heat is recovered by performing heat exchange with a heat medium (such as water). The temperature of the flue gas G having passed through the heat recovery facility 103 becomes, for example, 90° C. to 100° C., to improve dust collection capacity in an electronic precipitator 104.

The flue gas G having passed through the heat recovery facility 103 is introduced into the electronic precipitator 104, and dust is removed.

The flue gas G having passed through the electronic precipitator 104 is introduced into a desulfurization facility 105. In the desulfurization facility 105, sulfur oxide in the flue gas G is absorbed and removed by limestone ($CaCO_3$), and gypsum ($CaSO_4$, $2H_2O$) is formed as a by-product. The temperature of the flue gas G having passed through the desulfurization facility 105 generally decreases to about 50° C.

The flue gas G having passed through the desulfurization facility 105 is introduced into a reheating facility 106, which is the heat exchanger of the gas heater. The reheating facility 106 heats the flue gas G by recovered heat recovered by the heat recovery facility 103 in a process in which the heat medium is circulated between the heat recovery facility 103 and the reheating facility 106. At the temperature of about 50° C. having passed through the desulfurization facility 105, the flue gas G is hardly diffused due to a low temperature and may become white smoke. However, the flue gas G is reheated to 90° C. by the reheating facility 106 and released to the air from the stack 108 without generating white smoke.

The flue gas G having passed through the reheating facility 106 is introduced into a decarburization facility 107. In the decarburization facility 107, carbon dioxide ($CO_2$) in the flue gas G is absorbed by a limestone-containing absorbent (CaCO$_3$) to remove carbon dioxide from the flue gas G.

Figure 2:
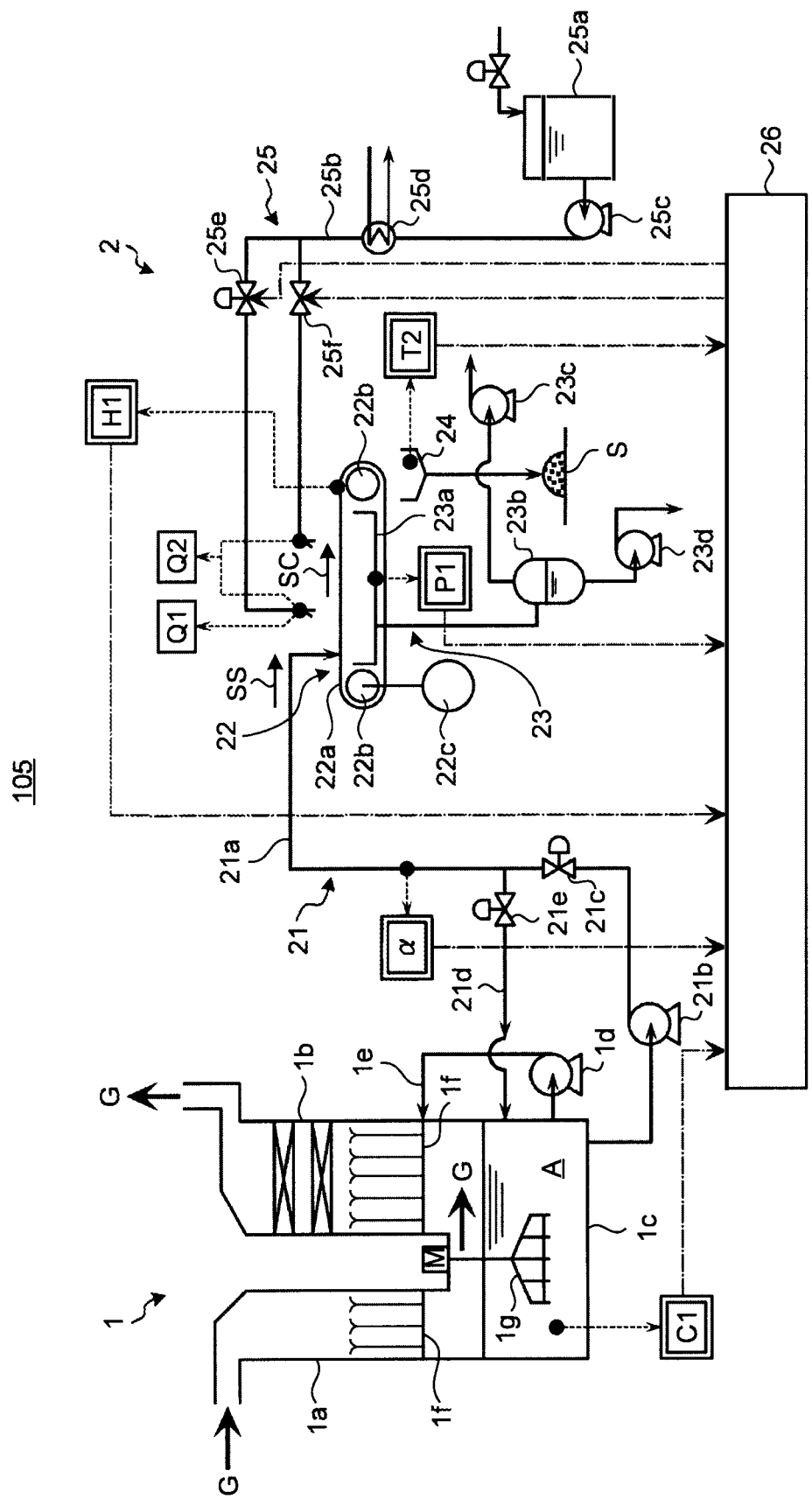
FIG. 2 is a schematic diagram of a gypsum dewatering device for a desulfurization facility according to a first embodiment of the present invention.

The desulfurization facility 105 is explained next with reference to the drawings. FIG. 2 is a schematic diagram of a gypsum dewatering device for a desulfurization facility according to the present embodiment. As shown in FIG. 2, in the desulfurization facility 105, a gypsum dewatering device 2 is attached to an absorber 1.

In the present embodiment, the absorber 1 is provided with an inlet-side liquid-jet column 1a that introduces the flue gas G from an upper part thereof and an outlet-side liquid-jet column 1b that discharges the desulfurized flue gas G from an upper part thereof in a row, and these columns are communicated with each other by a storage tank 1c at the bottoms thereof.

The absorber 1 stores a limestone-containing absorbent (hereinafter, "absorbent") A in the storage tank 1c. The absorbent A is pressure-fed by an absorbent circulating pump 1d, and fed to nozzles 1f in the respective liquid-jet columns 1a and 1b through an outside absorbent header 1e. The absorbent A fed to the nozzles 1f is injected upward in a liquid column form and then, flows down and is stored again in the storage tank 1c. A stirrer 1g is provided in the storage tank 1c, and the absorbent A is stirred by the stirrer 1g to prevent gypsum particles or limestone particles from settling in the absorbent A.

Meanwhile, the flue gas G is introduced from the upper part of the inlet-side liquid-jet column 1a to flow downward, passes through a cavity in the upper part of the storage tank 1c, and moves to the outlet-side liquid-jet column 1b. Thereafter, the flue gas G flows upward in the outlet-side liquid-jet column 1b. At this time, the absorbent A injected from the nozzles 1f and flowing downward is brought into countercurrent contact with the flue gas G flowing in the respective liquid-jet columns 1a and 1b. Therefore, sulfur oxide in the flue gas G is absorbed by the absorbent A and removed from the flue gas G. The flue gas G with sulfur oxide being removed is discharged from the upper part of the outlet-side liquid-jet column 1b and fed to the next facility.

The absorber is not limited to the configuration in which the two liquid-jet columns 1a and 1b are provided in a row. For example, the absorber can be constituted by a liquid-jet column in which the flue gas G is brought into contact with the absorbent while being introduced from the lower part thereof and discharged from the upper part thereof, although not shown. The contact between the absorbent A and the flue gas G includes co-current contact in which the flue gas G is caused to flow in parallel with the absorbent A flowing downward or countercurrent/co-current contact in which countercurrent contact and co-current contact are combined, other than the countercurrent contact described above.

The gypsum dewatering device 2 includes an extraction unit 21 that extracts gypsum slurry SS, from which sulfur oxide is absorbed by the absorbent A, from the storage tank 1c of the absorber 1, a belt filter 22 that dewaters the gypsum slurry SS fed from the extraction unit 21 to form a gypsum cake SC having a uniform thickness, and a vacuum suction mechanism 23 that sucks moisture from the gypsum cake SC dewatered by the belt filter 22.

The extraction unit 21 is provided with an extraction pump 21b in the middle of an extraction pipe 21a connected to the storage tank 1c at one end, with the other end extending to the belt filter 22. That is, the gypsum slurry SS in the storage tank 1c is pressure-fed by the extraction pump 21b and fed to the belt filter 22 through the extraction pipe 21a. A valve 21c is provided in the extraction pipe 21a on a downstream side of the extraction pump 21b. The valve 21c increases or decreases a flow rate of the gypsum slurry SS passing through the extraction pipe 21a, thereby adjusting a feed rate of the gypsum slurry SS to the belt filter 22. Furthermore, a return pipe 21d is provided on a downstream side of the valve 21c, which is branched and connected to the storage tank 1c. The return pipe 21d returns a part of the gypsum slurry SS extracted from the storage tank 1c through the extraction pipe 21a to the storage tank 1c. A valve 21e is provided in the return pipe 21d. The valve 21e increases or decreases the flow rate of the gypsum slurry SS to be returned to the storage tank 1c through the return pipe 21d, thereby adjusting an amount of the gypsum slurry SS returned to the storage tank 1c.

The belt filter 22 includes a belt 22a in which a filter made of a filter fabric is formed in an endless belt, at least one pair of rollers 22b for spanning the belt 22a, and a drive unit 22c such as a motor that rotates the rollers 22b to rotate the belt 22a. The gypsum slurry SS is fed onto the belt 22a by the extraction unit 21. Consequently, the gypsum slurry SS is carried in a rotation direction of the belt 22a. Although not shown, the belt filter 22 is configured so as to dewater the gypsum slurry SS on an upstream side of the belt 22a at which the gypsum slurry SS is fed, to form the gypsum cake SC having a uniform thickness. In second, third, and fourth embodiments described later, the drive unit 22c is constituted as a speed varying means that varies a belt advancing rate of the belt filter 22.

The vacuum suction mechanism 23 includes a suction port 23a provided in a space formed by the belt 22a of the belt filter 22 spanned by the rollers 22b in a range where the gypsum slurry SS is dewatered by the belt filter 22 as the gypsum cake SC, a gas-liquid separator 23b connected to the suction port 23a by a pipe, and an air suction pump 23c and a water suction pump 23d connected to the gas-liquid separator 23b by a pipe. That is, a negative pressure is applied to the suction port 23a by the air suction pump 23c via the gas-liquid separator 23b, thereby sucking moisture from the gypsum cake SC to be dewatered by the belt filter 22. Sucked moisture is stored in a lower part of the tank of the gas-liquid separator 23b from the suction port 23a. The air suction pump 23c is connected to an upper part of the tank of the gas-liquid separator 23b, and does not suck moisture stored in the lower part of the tank. On the other hand, moisture stored in the lower part of the tank of the gas-liquid separator 23b is sucked and discharged by the water suction pump 23d connected to the lower part of the tank.

As described above, the gypsum dewatering device 2 extracts the gypsum slurry SS from the storage tank 1c of the absorber 1 by the extraction unit 21, dewaters the gypsum slurry SS by the belt filter 22 to form the gypsum cake SC, and sucks moisture in the gypsum cake SC by the vacuum suction mechanism 23, thereby acquiring dewatered gypsum S. Furthermore, a hopper 24 that receives the dewatered gypsum S is provided on a downstream side of the belt filter 22, and the gypsum S is discharged from the hopper 24.

The gypsum dewatering device 2 according to the present embodiment includes a heating means 25 that heats the gypsum cake SC dewatered by the belt filter 22. The heating means 25 includes a hot water heating type that sprays hot water to the gypsum cake SC and a steam heating type that sprays steam to the gypsum cake SC.

The heating means 25 of the hot water heating type includes a water tank 25a that stores water supplied from water supply via a flow-rate adjusting valve, a feeding pipe 25b connected to the water tank 25a at one end and provided with a nozzle at the other end extending to the belt filter 22, a water supply pump 25c provided in the middle of the feeding pipe 25b, and a heating unit 25d provided in the middle of the feeding pipe 25b to heat water in the feeding pipe 25b by the heat of steam. The other end of the feeding pipe 25b is branched into a plurality of numbers (two in the present embodiment). The branched other ends of the feeding pipe 25b are provided so that nozzles are arranged in multiple stages (two stages in the present embodiment) along a transport direction of the gypsum cake SC to be dewatered by the belt filter 22. Although not shown, in the nozzle of the feeding pipe 25b, a plurality of injection ports are provided in a nozzle pipe arranged orthogonally to the transport direction of the gypsum cake SC to be dewatered by the belt filter 22, corresponding to a width direction of the gypsum cake SC. A flow-rate adjusting valve 25e and an opening and closing valve 25f are provided at the branched other ends of the feeding pipe 25b. The flow-rate adjusting valve 25e is provided on at least one side of the branched other ends of the feeding pipe 25b. The opening and closing valve 25f is provided at the other end.

In the heating means 25 of the hot water heating type, water stored in the water tank 25a is heated by the heating unit 25d to become hot water in a process of reaching the belt filter 22 via the feeding pipe 25b by the water supply pump 25c, injected to the gypsum cake SC on the belt filter 22 from the nozzle to heat the gypsum cake SC. Because the other end of the feeding pipe 25b is branched into a plurality of numbers, and the nozzles are provided in multiple stages along the transport direction of the gypsum cake SC, the heating means 25 injects hot water from the multistage nozzles to increase a heating temperature for heating the gypsum cake SC (Q2). Furthermore, the flow-rate adjusting valve 25e increases a flow rate of hot water injected from the nozzles to increase the heating temperature for heating the gypsum cake SC (Q1). Furthermore, hot water is injected from the multistage nozzles and the flow-rate adjusting valve 25e increases the flow rate of hot water injected from the nozzles, thereby increasing the temperature of the gypsum cake SC (Q1+Q2).

The heating means 25 of the steam heating type directly supplies steam of the heating unit 25d to the feeding pipe 25b. In the heating means 25 of the steam heating type, steam of the heating unit 25d is injected from the nozzles to the gypsum cake SC on the belt filter 22 to heat the gypsum cake SC. In the heating means 25, because the other end of the feeding pipe 25b is branched into a plurality of numbers, and the nozzles are provided in multiple stages along the transport direction of the gypsum cake SC, the heating temperature for heating the gypsum cake SC is increased by injecting steam from the multistage nozzles (Q2). Furthermore, the flow-rate adjusting valve 25e increases the flow rate of steam injected from the nozzles to increase the heating temperature for heating the gypsum cake SC (Q1). Furthermore, steam is injected from the multistage nozzles, and the flow-rate adjusting valve 25e increases the flow rate of steam injected from the nozzles to increase the temperature of the gypsum cake SC (Q1+Q2).

The gypsum dewatering device 2 includes a moisture measuring means H1 that measures a moisture content of the gypsum cake SC to be dewatered by the belt filter 22. As the moisture measuring means H1, for example, there is an infrared type that measures moisture in a non-contact manner. The moisture measuring means H1 is arranged immediately before the gypsum S dewatered by the belt filter 22 is fed to the hopper 24.

The gypsum dewatering device 2 includes a suction-pressure measuring means P1 that measures a vacuum pressure of the belt filter 22, that is, a suction pressure of the air suction pump 23c in the vacuum suction mechanism 23.

The gypsum dewatering device 2 also includes an impurity salt concentration measuring means C1 that measures a salt concentration as impurities in the absorbent A of the absorber 1. The impurities include, for example, Cl and Mg, and the impurity salt concentration measuring means C1 measures the salt concentration thereof. The impurity salt concentration measuring means C1 acquires correlation between conductivity and a salt concentration of the absorbent A in the absorber 1 in advance, and estimates the salt concentration by measuring conductivity.

The gypsum dewatering device 2 also includes a specific resistance-to-filtration measuring means α that measures a specific resistance to filtration of the gypsum cake SC. The specific resistance-to-filtration measuring means α is provided in the middle of the extraction pipe 21a of the extraction unit 21, and extracts a part of the gypsum slurry SS circulated in the extraction pipe 21a to measure the specific resistance to filtration, that is, ease of filtration according to a well-known equation.

Furthermore, the gypsum dewatering device 2 includes a surface-temperature measuring means T2 that measures the surface temperature of the gypsum cake SC. As the surface-temperature measuring means T2, for example, there is an infrared type that measures the surface temperature in a non-contact manner. The surface-temperature measuring means T2 is arranged in the hopper 24 that receives the gypsum S immediately after being dewatered by the belt filter 22.

Measurement data of the moisture measuring means H1, the suction-pressure measuring means P1, the impurity salt concentration measuring means C1, the specific resistance-to-filtration measuring means α, and the surface-temperature measuring means T2 are input to a control means 26. The control means 26 is a computer or the like. The control means 26 includes a RAM, a ROM and the like, and is provided with a storage unit (not shown) in which a program and data are stored. The data to be stored in the storage unit includes set values corresponding to values measured by the moisture measuring means H1, the suction-pressure measuring means P1, the impurity salt concentration measuring means C1, the specific resistance-to-filtration measuring means α, and the surface-temperature measuring means T2. The set value of the moisture measuring means H1 is, for example, 10 wt %, and indicates a quality standard of the gypsum S. The set values of the suction-pressure measuring means P1, the impurity salt concentration measuring means C1, and the specific resistance-to-filtration measuring means α are set at the time of operating the gypsum dewatering device 2 to satisfy the quality standard of the gypsum S. The flow-rate adjusting valve 25e and the opening and closing valve 25f of the heating means 25 are connected to the control means 26. The control means 26 controls the flow-rate adjusting valve 25e and the opening and closing valve 25f of the heating means 25 according to the program and data stored in the storage unit, based on input values from the moisture measuring means H1, the suction-pressure measuring means P1, the impurity salt concentration measuring means C1, the specific resistance-to-filtration measuring means α, and the surface-temperature measuring means T2.

Control by the control means 26 is explained below with reference to a flowchart in FIG. 3.

Figure 3:
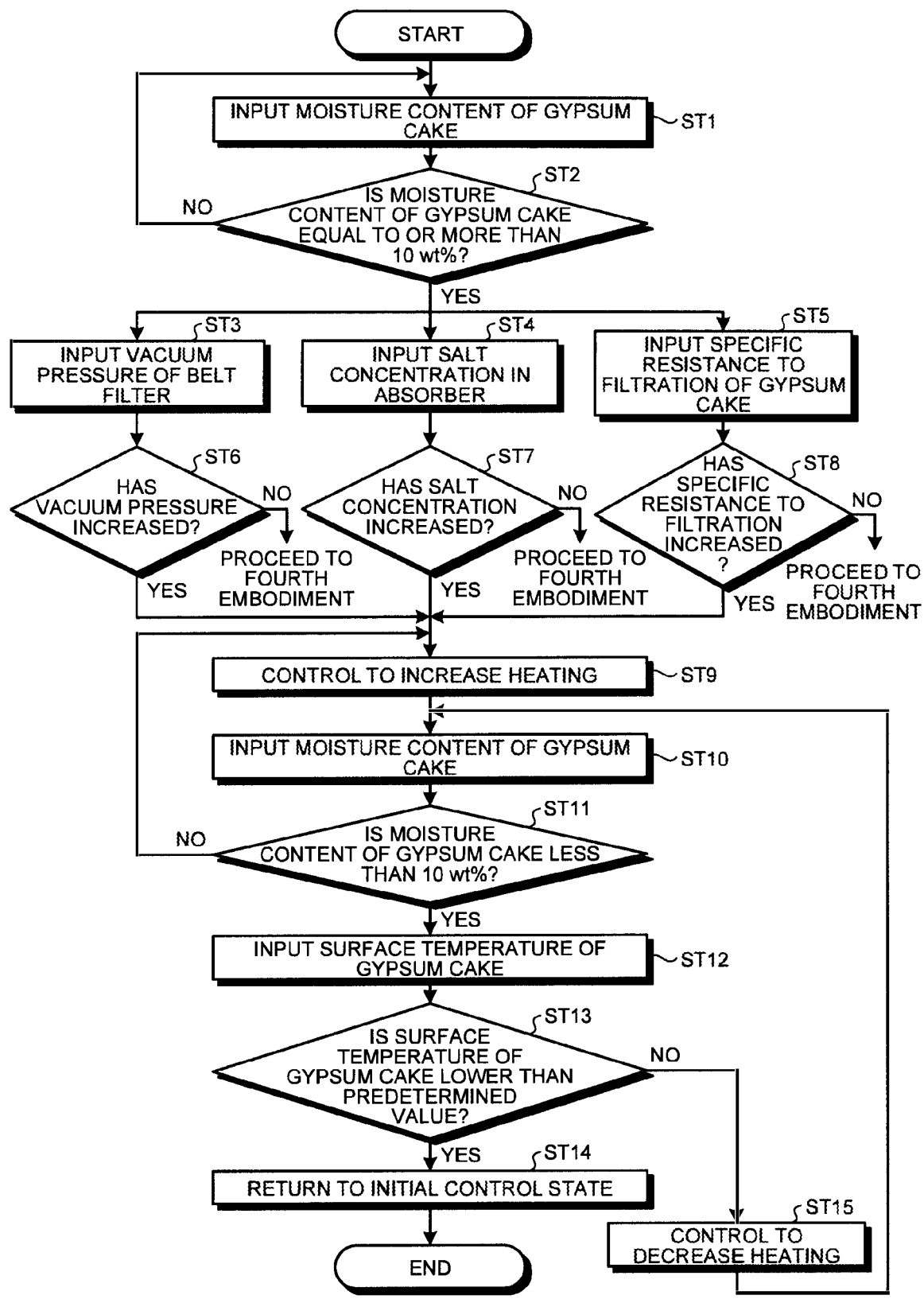
FIG. 3 is a flowchart of control by the gypsum dewatering device for a desulfurization facility according to the first embodiment of the present invention.

As shown in FIG. 3, the control means 26 first inputs a moisture content of the gypsum cake SC from the moisture measuring means H1 (Step ST1). When the input moisture content of the gypsum cake SC is equal to or more than 10 wt %, which is the set value (YES at Step ST2), the control means 26 inputs a vacuum pressure of the belt filter 22 from the suction-pressure measuring means P1 (Step ST3), inputs a salt concentration in the absorber 1 from the impurity salt concentration measuring means C1 (Step ST4), and inputs a specific resistance to filtration of the gypsum cake SC from the specific resistance-to-filtration measuring means α (Step ST5). When the vacuum pressure has increased more than the set value (YES at Step ST6), the salt concentration has increased more than the set value (YES at Step ST7), or the specific resistance to filtration has increased more than the set value (YES at Step ST8), the control means 26 controls to increase heating by the heating means 25 (Step ST9). That is, the control means 26 controls the flow-rate adjusting valve 25e and the opening and closing valve 25f in an opening direction and increases the heating temperature for heating the gypsum cake SC by spraying hot water or steam from the multistage nozzles (Q2), by increasing the flow rate of hot water or steam sprayed from the nozzles (Q1), or by spraying hot water or steam from the multistage nozzles and increasing the flow rate of hot water or steam sprayed from the nozzles (Q1+Q2).

Because the heating temperature for heating the gypsum cake SC is increased to dissolve salt, water viscosity decreases, and the moisture suction property from the gypsum cake SC is improved so as to restore the dewatering performance.

The control means 26 then inputs a moisture content of the gypsum cake SC from the moisture measuring means H1 (Step ST10). When the input moisture content of the gypsum cake SC is less than 10 wt % as the set value (YES at Step ST11), the control means 26 inputs the surface temperature of the gypsum cake SC from the surface-temperature measuring means T2 (Step ST12). When the surface temperature of the gypsum cake SC is lower than a predetermined value (YES at Step ST13), the control means 26 returns the heating means 25 to an initial control state (Step ST14), to finish the control.

Meanwhile, at Step ST13, when the surface temperature of the gypsum cake SC is not lower than the predetermined value (NO at Step ST13), the control means 26 controls to decrease heating by the heating means 25 (Step ST15). That is, the control means 26 controls the flow-rate adjusting valve 25e and the opening and closing valve 25f in a closing direction, and decreases the heating temperature for heating the gypsum cake SC by decreasing the number of stages of the nozzles, by decreasing the flow rate of hot water or steam sprayed from the nozzles, or by decreasing the number of stages of the nozzles and decreasing the flow rate of hot water or steam sprayed from the nozzles. The control means 26 then returns to Step ST10, to input the moisture content of the gypsum cake SC from the moisture measuring means H1.

Particularly, excessive moisture due to condensation of steam is prevented by maintaining the surface temperature of the gypsum cake SC to be equal to or lower than the predetermined value, thereby enabling to avoid a state of increasing moisture in the gypsum cake SC.

At Step ST11, when the input moisture content of the gypsum cake SC is not less than 10 wt % as the set value (NO at Step ST11), control returns to Step ST9. Furthermore, when the vacuum pressure has not increased more than the set value at Step ST6 (NO at Step ST6), when the salt concentration has not increased more than the set value at Step ST7 (NO at Step ST7), and when the specific resistance to filtration has not increased more than the set value at Step ST8 (NO at Step ST8), control proceeds to control according to a fourth embodiment described later.

As described above, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures a suction pressure by the vacuum suction mechanism 23, the impurity salt concentration measuring means C1 that measures a salt concentration as impurities in the absorber 1, the specific resistance-to-filtration measuring unit α that measures a specific resistance to filtration of the gypsum cake SC, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount, and an input value from at least one of the suction-pressure measuring means P1, the impurity salt concentration measuring means C1, and the specific resistance-to-filtration measuring unit α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1, the impurity salt concentration measuring means C1, and the specific resistance-to-filtration measuring means α.

In the control by the control means 26 described above, at Step ST2, when the input moisture content of the gypsum cake SC is equal to or more than 10 wt % as the set value (YES at Step ST2), the control means 26 inputs only the vacuum pressure of the belt filter 22 from the suction-pressure measuring means P1 (Step ST3), and may not perform input of the salt concentration in the absorber 1 from the impurity salt concentration measuring means C1 (Step ST4), and input of the specific resistance to filtration of the gypsum cake SC from the specific resistance-to-filtration measuring means α (Step ST5). That is, control is performed by the input of the vacuum pressure of the belt filter 22 from the suction-pressure measuring means P1.

That is, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures a suction pressure by the vacuum suction mechanism 23, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount, and an input value from the suction-pressure measuring means P1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the suction-pressure measuring means P1.

In the control by the control means 26 described above, at Step ST2, when the input moisture content of the gypsum cake SC is equal to or more than 10 wt % as the set value (YES at Step ST2), the control means 26 inputs only the salt concentration in the absorber 1 from the impurity salt concentration measuring means C1 (Step ST4), and may not perform input of the vacuum pressure of the belt filter 22 from the suction-pressure measuring means P1 (Step ST3), and input of the specific resistance to filtration of the gypsum cake SC from the specific resistance-to-filtration measuring means α (Step ST5). That is, control is performed by the input of the salt concentration in the absorber 1 from the impurity salt concentration measuring means C1.

As described above, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the impurity salt concentration measuring means C1 that measures a salt concentration as impurities in the absorber 1, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount, and an input value from the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the impurity salt concentration measuring means C1.

In the control by the control means 26 described above, at Step ST2, when the input moisture content of the gypsum cake SC is equal to or more than 10 wt % as the set value (YES at Step ST2), the control means 26 inputs only the specific resistance to filtration of the gypsum cake SC from the specific resistance-to-filtration measuring means α (Step ST5) and may not perform input of the vacuum pressure of the belt filter 22 from the suction-pressure measuring means P1 (Step ST3), and input of the salt concentration in the absorber 1 from the impurity salt concentration measuring means C1 (Step ST4). That is, control is performed by the input of the specific resistance to filtration of the gypsum cake SC from the specific resistance-to-filtration measuring means α.

As described above, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the specific resistance-to-filtration measuring means α that measures the specific resistance to filtration of the gypsum cake SC, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount, and an input value from the specific resistance-to-filtration measuring means α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the specific resistance-to-filtration measuring means α.

In the control by the control means 26 described above, at Step ST2, when the input moisture content of the gypsum cake SC is equal to or more than 10 wt % as the set value (YES at Step ST2), the control means 26 inputs the vacuum pressure of the belt filter 22 from the suction-pressure measuring means P1 (Step ST3) and the salt concentration in the absorber 1 from the impurity salt concentration measuring means C1 (Step ST4), and may not perform input of the specific resistance to filtration of the gypsum cake SC from the specific resistance-to-filtration measuring means α (Step ST5). That is, control is performed by the input of the suction pressure of the belt filter 22 from the suction-pressure measuring means P1 and the input of the salt concentration in the absorber 1 from the impurity salt concentration measuring means C1.

As described above, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures the suction pressure by the vacuum suction mechanism 23, the impurity salt concentration measuring means C1 that measures a salt concentration as impurities in the absorber 1, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount, and an input value from at least one of the suction-pressure measuring means P1 and the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1 and the impurity salt concentration measuring means C1.

In the control by the control means 26 described above, at Step ST2, when the input moisture content of the gypsum cake SC is equal to or more than 10 wt % as the set value (YES at Step ST2), the control means 26 can proceed to Step ST9 to perform control to increase heating by the heating means 25. That is, control at Steps ST3 to ST8 may not be performed.

As described above, the gypsum dewatering device for a desulfurization facility according to the first embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the heating means 25 that heats the gypsum cake SC dewatered by the belt filter 22 by hot water or steam, and the control means 26 that controls a heated state by the heating means 25, when the moisture content of the gypsum cake SC input from the moisture measuring means H1 has exceeded a predetermined amount.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained.

Second Embodiment

Figure 4:
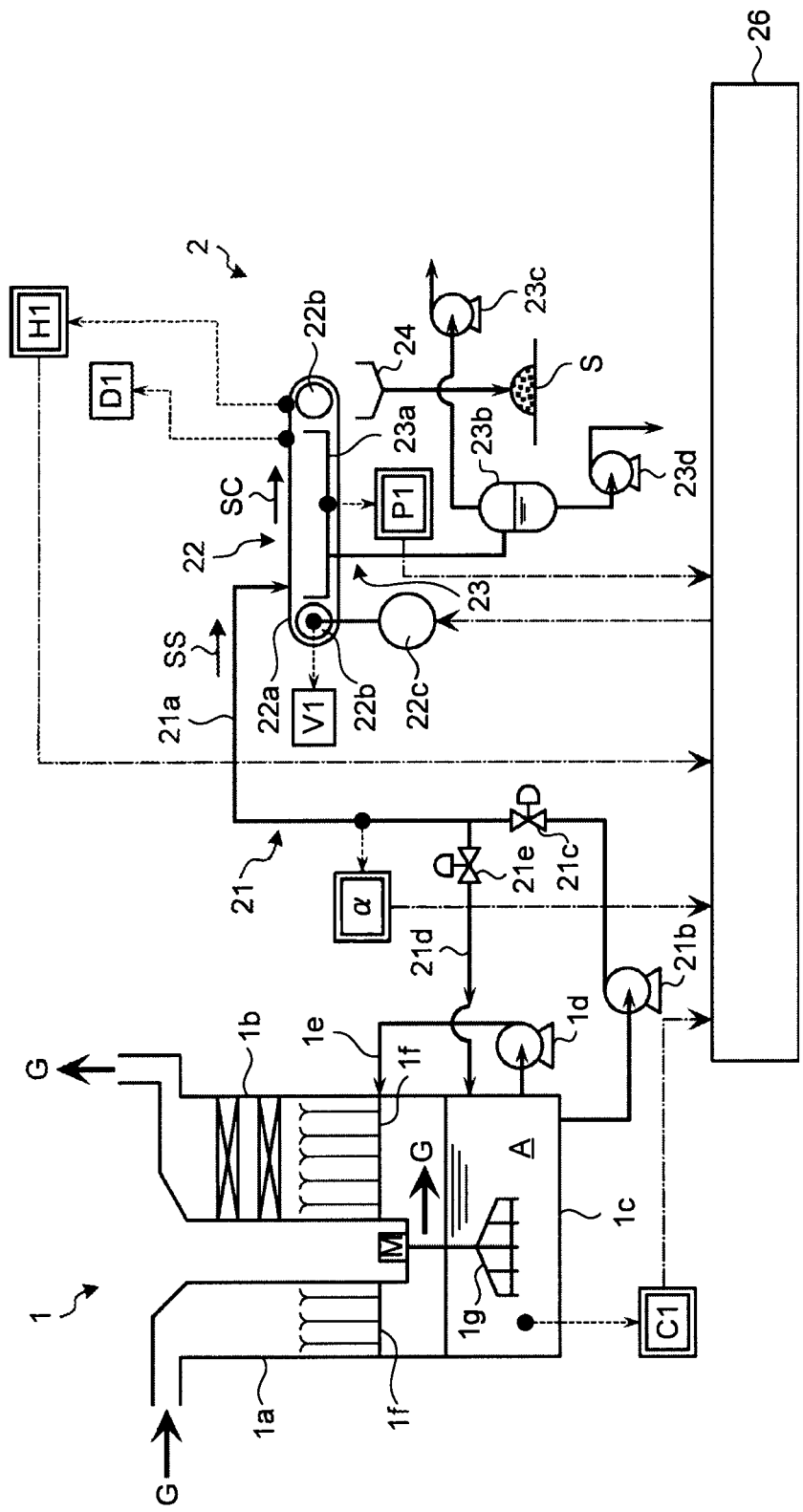
FIG. 4 is a schematic diagram of a gypsum dewatering device for a desulfurization facility according to a second embodiment of the present invention.

The second embodiment of the present invention is explained with reference to the drawings. FIG. 4 is a schematic diagram of a gypsum dewatering device for a desulfurization facility according to the present embodiment. In the second embodiment explained below, constituent elements equivalent to those of the first embodiment are denoted by like reference signs and explanations thereof will be omitted.

As shown in FIG. 4, the gypsum dewatering device 2 according to the present embodiment does not include the heating means 25 in the desulfurization facility according to the first embodiment. In the belt filter 22 of the gypsum dewatering device 2, the drive unit 22c is constituted as a speed varying means that varies the rotation speed of the rollers 22b, thereby varying a belt advancing rate of the belt 22a. The speed varying means accelerates the rotation speed of the rollers 22b to accelerate the belt advancing rate (V1), thereby decreasing the thickness (D1) of the gypsum cake SC. In contrast, the speed varying means decelerates the rotation speed of the rollers 22b to decrease the belt advancing rate (V1), thereby increasing the thickness (D1) of the gypsum cake SC.

The gypsum dewatering device 2 includes the moisture measuring means H1 that measures a moisture content of the gypsum cake SC to be dewatered by the belt filter 22. As the moisture measuring means H1, for example, there is an infrared type that measures moisture in a non-contact manner. The moisture measuring means H1 is arranged immediately before the gypsum S dewatered by the belt filter 22 is fed to the hopper 24.

The gypsum dewatering device 2 also includes the suction-pressure measuring means P1 that measures a vacuum pressure of the belt filter 22, that is, a suction pressure of the air suction pump 23c in the vacuum suction mechanism 23.

The gypsum dewatering device 2 also includes the impurity salt concentration measuring means C1 that measures a salt concentration as impurities in the absorbent A of the absorber 1. The impurities include, for example, Cl and Mg, and the impurity salt concentration measuring means C1 measures the salt concentration thereof. The impurity salt concentration measuring means C1 acquires correlation between conductivity and a salt concentration of the absorbent A in the absorber 1 in advance, and estimates the salt concentration by measuring conductivity.

The gypsum dewatering device 2 also includes the specific resistance-to-filtration measuring means α that measures a specific resistance to filtration of the gypsum cake SC. The specific resistance-to-filtration measuring means α is provided in the middle of the extraction pipe 21a of the extraction unit 21, and extracts a part of the gypsum slurry SS circulated in the extraction pipe 21a to measure the specific resistance to filtration, that is, ease of filtration according to a well-known equation.

Measurement data of the moisture measuring means H1, the suction-pressure measuring means P1, the impurity salt concentration measuring means C1, and the specific resistance-to-filtration measuring means α are input to the control means 26. The control means 26 is a computer or the like. The control means 26 includes a RAM, a ROM and the like, and is provided with a storage unit (not shown) in which a program and data are stored. The data to be stored in the storage unit includes set values corresponding to values measured by the moisture measuring means H1, the suction-pressure measuring means P1, the impurity salt concentration measuring means C1, and the specific resistance-to-filtration measuring means α. The set value of the moisture measuring means H1 is, for example, 10 wt %, and indicates a quality standard of the gypsum S. The set values of the suction-pressure measuring means P1, the impurity salt concentration measuring means C1, and the specific resistance-to-filtration measuring means α are set at the time of operating the gypsum dewatering device 2 to satisfy the quality standard of the gypsum S. The drive unit (the speed varying means) 22c of the belt filter 22 is connected to the control means 26. The control means 26 controls the drive unit 22c of the belt filter 22 according to the program and data stored in the storage unit, based on the input values from the moisture measuring means H1, the suction-pressure measuring means P1, the impurity salt concentration measuring means C1, and the specific resistance-to-filtration measuring means α.

Control by the control means 26 is explained below with reference to a flowchart in FIG. 5.

Figure 5:
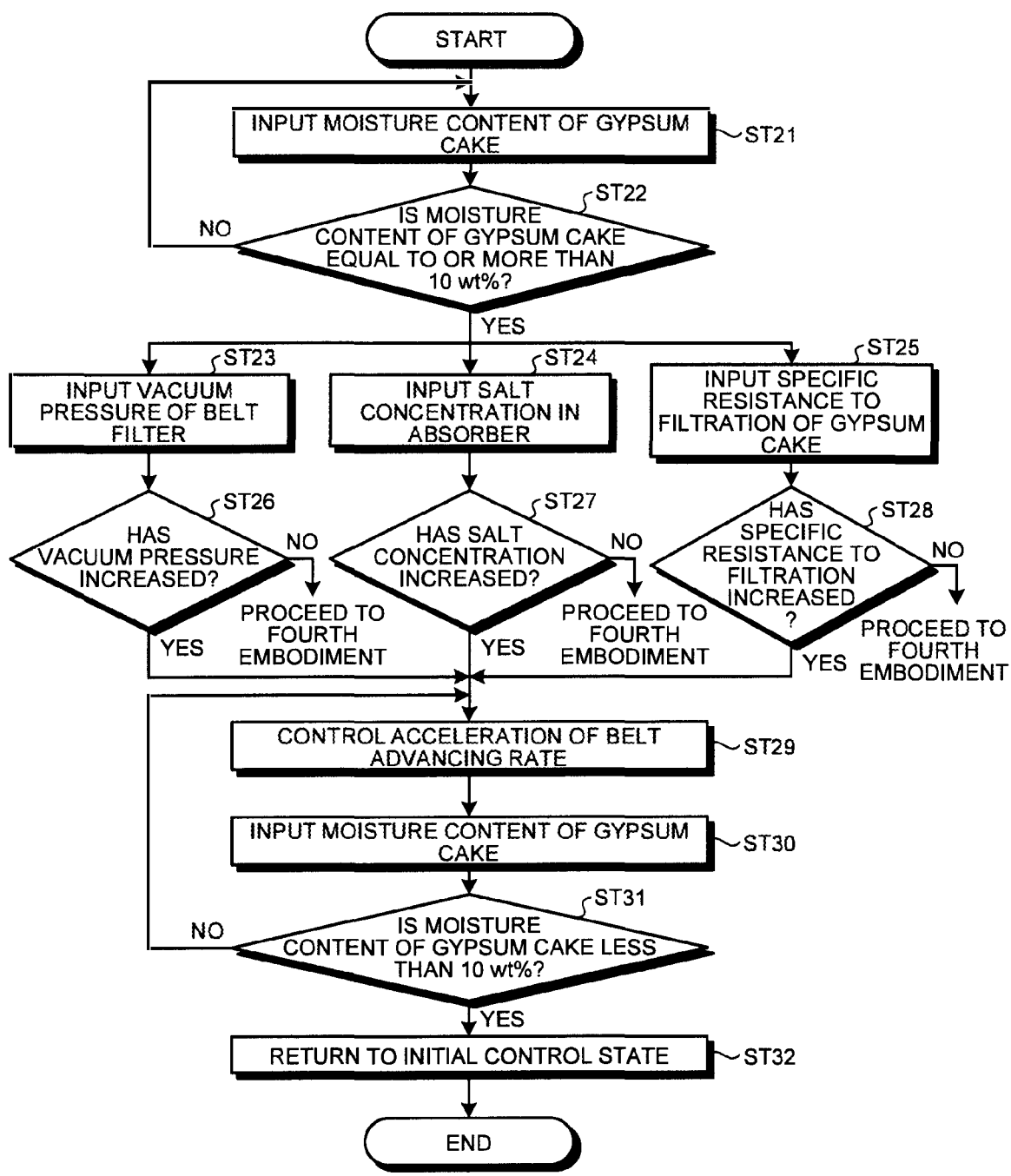
FIG. 5 is a flowchart of control by the gypsum dewatering device for a desulfurization facility according to the second embodiment of the present invention.

As shown in FIG. 5, the control means 26 first inputs a moisture content of the gypsum cake SC from the moisture measuring means H1 (Step ST21). When the input moisture content of the gypsum cake SC is equal to or more than 10 wt %, which is the set value (YES at Step ST22), the control means 26 inputs a vacuum pressure of the belt filter 22 from the suction-pressure measuring means P1 (Step ST23), inputs a salt concentration in the absorber 1 from the impurity salt concentration measuring means C1 (Step ST24), and inputs a specific resistance to filtration of the gypsum cake SC from the specific resistance-to-filtration measuring means α (Step ST25). When the vacuum pressure has increased more than the set value (YES at Step ST26), the salt concentration has increased more than the set value (YES at Step ST27), or the specific resistance to filtration has increased more than the set value (YES at Step ST28), the control means 26 controls the belt advancing rate by the speed varying means (Step ST29). That is, the control means 26 accelerates the rotation speed of the rollers 22b by controlling the drive unit 22c of the belt filter 22 to accelerate the belt advancing rate (V1), thereby decreasing a thickness (D1) of the gypsum cake SC.

When the thickness (D1) of the gypsum cake SC is decreased, the specific resistance to filtration decreases, and thus the dewatering performance is restored.

The control means 26 inputs a moisture content of the gypsum cake SC from the moisture measuring means H1 (Step ST30). When the input moisture content of the gypsum cake SC is less than 10 wt % as the set value (YES at Step ST31), the control means 26 returns the speed varying means to an initial control state (Step ST32), to finish the control.

At Step ST31, when the input moisture content of the gypsum cake SC is not less than 10 wt % as the set value (NO at Step ST31), control returns to Step ST29. Furthermore, when the vacuum pressure has not increased more than the set value at Step ST26 (NO at Step ST26), when a salt concentration has not increased more than the set value at Step ST27 (NO at Step ST27), and when the specific resistance to filtration has not increased more than the set value at Step ST28 (NO at Step ST28), control proceeds to control according to the fourth embodiment described later.

As described above, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures a suction pressure by the vacuum suction mechanism 23, the impurity salt concentration measuring means C1 that measures a salt concentration as impurities in the absorber 1, the specific resistance-to-filtration measuring unit α that measures a specific resistance to filtration of the gypsum cake SC, the speed varying means (the drive unit 22c) that varies the belt advancing rate of the belt filter 22, and the control means 26 that controls the belt advancing rate by the speed varying means, when the moisture content of the gypsum cake SC input from the moisture measuring means H1 has exceeded a predetermined amount, and an input value from at least one of the suction-pressure measuring means P1, the impurity salt concentration measuring means C1, and the specific resistance-to-filtration measuring means α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1, the impurity salt concentration measuring means C1, and the specific resistance-to-filtration measuring means α.

In the control by the control means 26 described above, at Step ST22, when the input moisture content of the gypsum cake SC is equal to or more than 10 wt % as the set value (YES at Step ST22), the control means 26 inputs only the vacuum pressure of the belt filter 22 from the suction-pressure measuring means P1 (Step ST23), and may not perform input of the salt concentration in the absorber 1 from the impurity salt concentration measuring means C1 (Step ST24), and input of the specific resistance to filtration of the gypsum cake SC from the specific resistance-to-filtration measuring means α (Step ST25). That is, control is performed by the input of the vacuum pressure of the belt filter 22 from the suction-pressure measuring means P1.

That is, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device includes the moisture measuring means H1 that measures a moisture content of the gypsum cake SC to be dewatered by the belt filter 22, the suction-pressure measuring means P1 that measures a suction pressure by the vacuum suction mechanism 23, the speed varying means (the drive unit 22c) that varies the belt advancing rate of the belt filter 22, and the control means 26 that controls the belt advancing rate by the speed varying means, when the moisture content of the gypsum cake SC input from the moisture measuring means H1 has exceeded a predetermined amount, and an input value from the suction-pressure measuring means P1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the suction-pressure measuring means P1.

In the control by the control means 26 described above, at Step ST22, when the input moisture content of the gypsum cake SC is equal to or more than 10 wt % as the set value (YES at Step ST22), the control means 26 inputs only the salt concentration in the absorber 1 from the impurity salt concentration measuring means C1 (Step ST24) and may not perform input of the vacuum pressure of the belt filter 22 from the suction-pressure measuring means P1 (Step ST23), and input of the specific resistance to filtration of the gypsum cake SC from the specific resistance-to-filtration measuring means α (Step ST25). That is, control is performed by the input of the salt concentration in the absorber 1 from the impurity salt concentration measuring means C1.

As described above, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the impurity salt concentration measuring means C1 that measures a salt concentration as impurities in the absorber 1, the speed varying means (the drive unit 22*c*) that varies the belt advancing rate of the belt filter 22, and the control means 26 that controls the belt advancing rate by the speed varying means, when the moisture content of the gypsum cake SC input from the moisture measuring means H1 has exceeded a predetermined amount, and an input value from the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the impurity salt concentration measuring means C1.

In the control by the control means 26 described above, at Step ST22, when the input moisture content of the gypsum cake SC is equal to or more than 10 wt % as the set value (YES at Step ST22), the control means 26 inputs only the specific resistance to filtration of the gypsum cake SC from the specific resistance-to-filtration measuring means α (Step ST25) and may not perform input of the suction pressure of the belt filter 22 from the suction-pressure measuring means P1 (Step ST23) and input of the salt concentration in the absorber 1 from the impurity salt concentration measuring means C1 (Step ST24). That is, control is performed by the input of the specific resistance to filtration of the gypsum cake SC from the specific resistance-to-filtration measuring means α.

As described above, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the specific resistance-to-filtration measuring means α that measures a specific resistance to filtration of the gypsum cake SC, the speed varying means (the drive unit 22*c*) that varies the belt advancing rate of the belt filter 22, and the control means 26 that controls the belt advancing rate by the speed varying means, when the moisture content of the gypsum cake SC input from the moisture measuring means H1 has exceeded a predetermined amount, and an input value from the specific resistance-to-filtration measuring means α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the specific resistance-to-filtration measuring means α.

In the control by the control means 26 described above, at Step ST22, when the input moisture content of the gypsum cake SC is equal to or more than 10 wt % as the set value (YES at Step ST22), the control means 26 inputs the suction pressure of the belt filter 22 from the suction-pressure measuring means P1 (Step ST23) and the salt concentration in the absorber 1 from the impurity salt concentration measuring means C1 (Step ST24), and may not perform input of the specific resistance to filtration of the gypsum cake SC from the specific resistance-to-filtration measuring means α (Step ST25). That is, control is performed by the input of the suction pressure of the belt filter 22 from the suction-pressure measuring means P1 and the input of the salt concentration in the absorber 1 from the impurity salt concentration measuring means C1.

As described above, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures the suction pressure by the vacuum suction mechanism 23, the impurity salt concentration measuring means C1 that measures a salt concentration as impurities in the absorber 1, the speed varying means (the drive unit 22*c*) that varies the belt advancing rate of the belt filter 22, and the control means 26 that controls the belt advancing rate by the speed varying means when the moisture content of the gypsum cake SC input from the moisture measuring means H1 has exceeded a predetermined amount, and an input value from at least one of the suction-pressure measuring means P1 and the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1 and the impurity salt concentration measuring means C1.

In the control by the control means 26 described above, at Step ST2, when the input moisture content of the gypsum cake SC is equal to or more than 10 wt % as the set value (YES at Step ST2), the control means 26 can proceed to Step ST9 to perform control of the belt advancing rate by the speed varying means. That is, control at Steps ST23 to ST28 may not be performed.

As described above, the gypsum dewatering device for a desulfurization facility according to the second embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the speed varying means (the drive unit 22c) that varies the belt advancing rate of the belt filter 22, and the control means 26 that controls the belt advancing rate by the speed varying means, when the moisture content of the gypsum cake SC input from the moisture measuring means H1 has exceeded a predetermined amount.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained.

Third Embodiment

Figure 6:
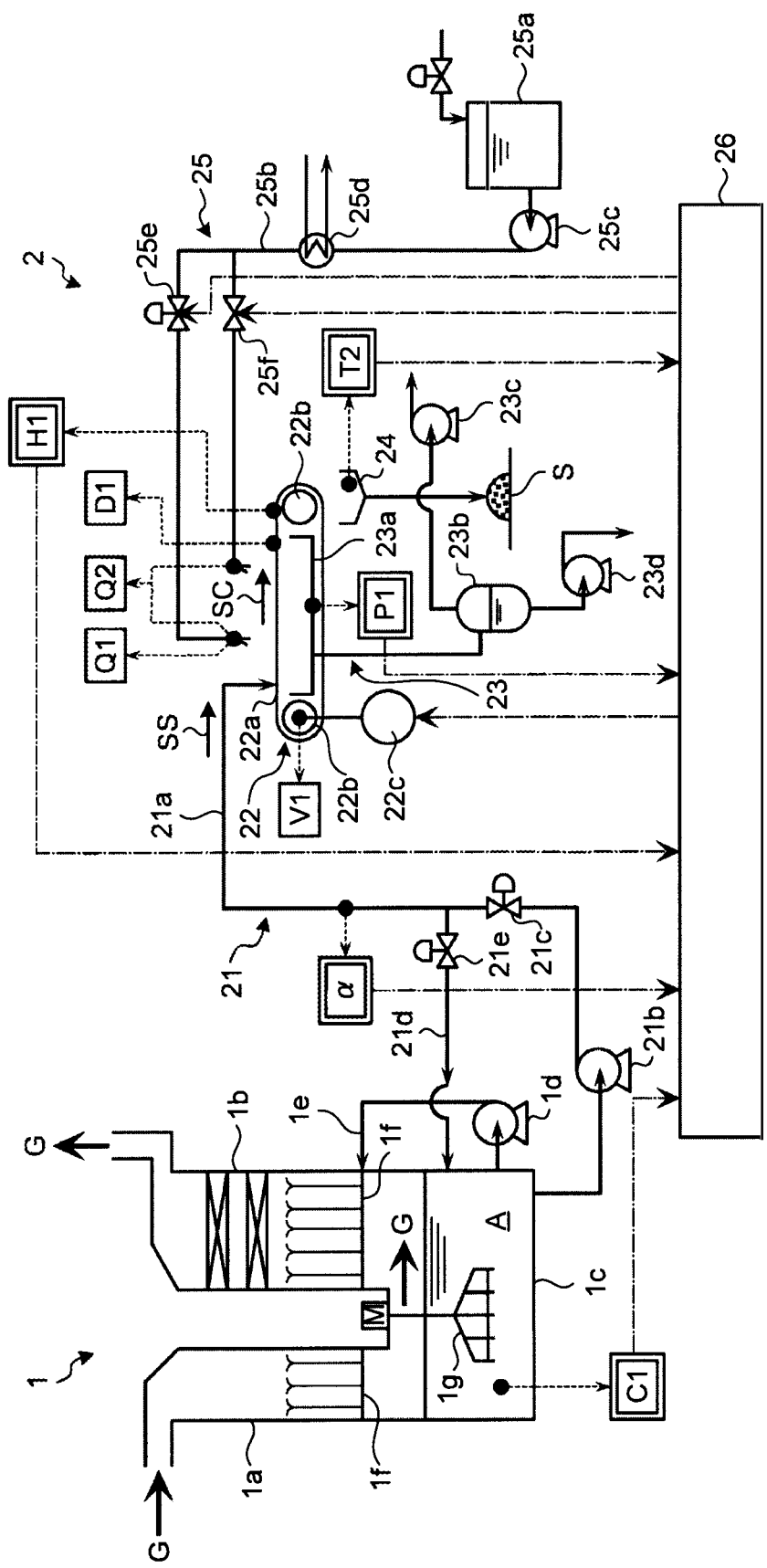
FIG. 6 is a schematic diagram of a gypsum dewatering device for a desulfurization facility according to a third embodiment of the present invention.

The third embodiment of the present invention is explained with reference to the drawings. FIG. 6 is a schematic diagram of a gypsum dewatering device for a desulfurization facility according to the present embodiment. In the third embodiment explained below, constituent elements equivalent to those of the first embodiment are denoted by like reference signs and explanations thereof will be omitted.

As shown in FIG. 6, the gypsum dewatering device 2 according to the present embodiment includes the heating means 25 in the gypsum dewatering device according to the first embodiment, and the speed varying means (the drive unit 22c) according to the second embodiment.

Furthermore, the gypsum dewatering device 2 includes the moisture measuring means H1 that measures a moisture content of the gypsum cake SC to be dewatered by the belt filter 22. As the moisture measuring means H1, for example, there is an infrared type that measures moisture in a non-contact manner. The moisture measuring means H1 is arranged immediately before the gypsum S dewatered by the belt filter 22 is fed to the hopper 24.

The gypsum dewatering device 2 includes the suction-pressure measuring means P1 that measures a vacuum pressure of the belt filter 22, that is, a suction pressure of the air suction pump 23c in the vacuum suction mechanism 23.

The gypsum dewatering device 2 also includes the impurity salt concentration measuring means C1 that measures a salt concentration as impurities in the absorbent A of the absorber 1. The impurities include, for example, Cl and Mg, and the impurity salt concentration measuring means C1 measures the salt concentration thereof. The impurity salt concentration measuring means C1 acquires correlation between conductivity and the salt concentration of the absorbent A in the absorber 1 in advance, and estimates the salt concentration by measuring conductivity.

The gypsum dewatering device 2 also includes the specific resistance-to-filtration measuring means α that measures a specific resistance to filtration of the gypsum cake SC. The specific resistance-to-filtration measuring means α is provided in the middle of the extraction pipe 21a of the extraction unit 21, and extracts a part of the gypsum slurry SS circulated in the extraction pipe 21a to measure the specific resistance to filtration, that is, ease of filtration according to a well-known equation.

Furthermore, the gypsum dewatering device 2 includes the surface-temperature measuring means T2 that measures the surface temperature of the gypsum cake SC. As the surface-temperature measuring means T2, for example, there is an infrared type that measures the surface temperature in a non-contact manner. The surface-temperature measuring means T2 is arranged in the hopper 24 that receives the gypsum S immediately after being dewatered by the belt filter 22.

Measurement data of the moisture measuring means H1, the suction-pressure measuring means P1, the impurity salt concentration measuring means C1, the specific resistance-to-filtration measuring means α, and the surface-temperature measuring means T2 are input to the control means 26. The control means 26 is a computer or the like. The control means 26 includes a RAM, a ROM and the like, and is provided with a storage unit (not shown) in which a program and data are stored. The data to be stored in the storage unit includes set values corresponding to values measured by the moisture measuring means H1, the suction-pressure measuring means P1, the impurity salt concentration measuring means C1, the specific resistance-to-filtration measuring means α, and the surface-temperature measuring means T2. The set value of the moisture measuring means H1 is, for example, 10 wt %, and indicates a quality standard of the gypsum S. The set values of the suction-pressure measuring means P1, the impurity salt concentration measuring means C1, and the specific resistance-to-filtration measuring means α are set at the time of operating the gypsum dewatering device 2 to satisfy the quality standard of the gypsum S. The control means 26 is connected to the flow-rate adjusting valve 25e and the opening and closing valve 25f of the heating means 25 and the drive unit (the speed varying means) 22c of the belt filter 22. The control means 26 controls the flow-rate adjusting valve 25e and the opening and closing valve 25f of the heating means 25 and the drive unit 22c of the belt filter 22 according to the program and data stored in the storage unit, based on the input values from the moisture measuring means H1, the suction-pressure measuring means P1, the impurity salt concentration measuring means C1, the specific resistance-to-filtration measuring means α, and the surface-temperature measuring means T2.

Control by the control means 26 is explained below with reference to a flowchart in FIG. 7.

Figure 7:
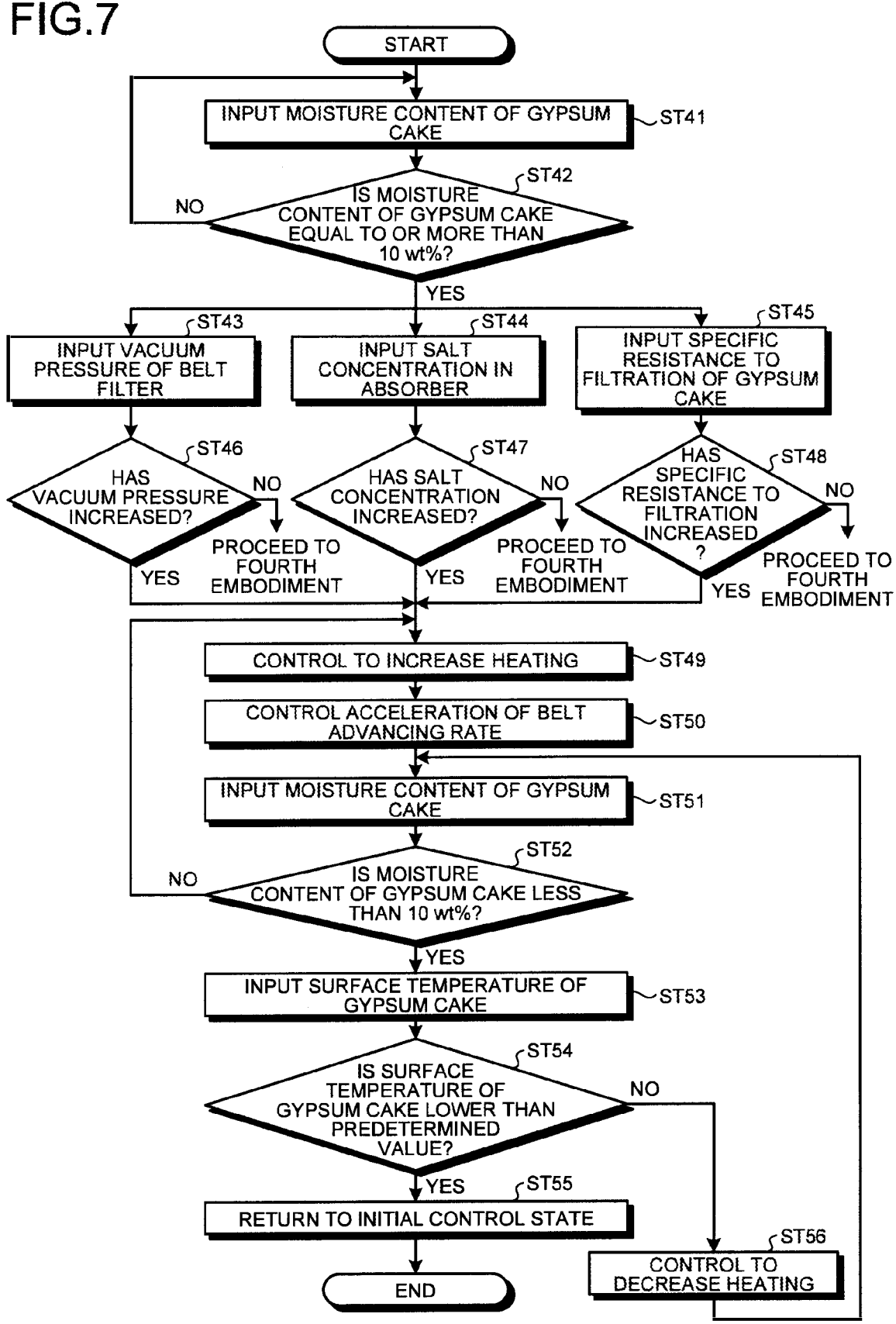
FIG. 7 is a flowchart of control by the gypsum dewatering device for a desulfurization facility according to the third embodiment of the present invention.

As shown in FIG. 7, the control means 26 first inputs a moisture content of the gypsum cake SC from the moisture measuring means H1 (Step ST41). When the input moisture content of the gypsum cake SC is equal to or more than 10 wt %, which is the set value (YES at Step ST42), the control means 26 inputs a vacuum pressure of the belt filter 22 from the suction-pressure measuring means P1 (Step ST43), inputs a salt concentration in the absorber 1 from the impurity salt concentration measuring means C1 (Step ST44), and inputs a specific resistance to filtration of the gypsum cake SC from the specific resistance-to-filtration measuring means α (Step ST45). When the vacuum pressure has increased more than the set value (YES at Step ST46), the salt concentration has increased more than the set value (YES at Step ST47), or the specific resistance to filtration has increased more than the set value (YES at Step ST48), the control means 26 controls to increase heating by the heating means 25 (Step ST49). That is, the control means 26 controls the flow-rate adjusting valve 25e and the opening and closing valve 25f in an opening direction and increases a heating temperature for heating the gypsum cake SC by spraying hot water or steam from the multistage nozzles (Q2), by increasing a flow rate of hot water or steam sprayed from the nozzles (Q1), or by spraying hot water or steam from the multistage nozzles and increasing the flow rate of hot water or steam sprayed from the nozzles (Q1+Q2). Furthermore, the control means 26 controls a belt advancing rate by the speed varying means (Step ST50). That is, the control means 26 accelerates the rotation speed of the rollers 22b by controlling the drive unit 22c of the belt filter 22 to accelerate the belt advancing rate (V1), thereby decreasing the thickness (D1) of the gypsum cake SC.

Because the heating temperature for heating the gypsum cake SC is increased to dissolve salt, water viscosity decreases, and the moisture suction property from the gypsum cake SC is improved so as to restore the dewatering performance. Furthermore, when the thickness (D1) of the gypsum cake SC is decreased, the specific resistance to filtration also decreases, thereby restoring the dewatering performance.

The control means 26 then inputs a moisture content of the gypsum cake SC from the moisture measuring means H1 (Step ST51). When the input moisture content of the gypsum cake SC is less than 10 wt % as the set value (YES at Step ST52), the control means 26 inputs the surface temperature of the gypsum cake SC from the surface-temperature measuring means T2 (Step ST53). When the surface temperature of the gypsum cake SC is lower than a predetermined value (YES at Step ST54), the control means 26 returns the heating means 25 and the speed varying means to initial control states (Step ST55), to finish the control.

On the other hand, at Step ST54, when the surface temperature of the gypsum cake SC is not lower than the predetermined value (NO at Step ST54), the control means 26 controls to decrease heating by the heating means 25 (Step ST56). That is, the control means 26 controls the flow-rate adjusting valve 25e and the opening and closing valve 25f in a closing direction, and decreases the heating temperature for heating the gypsum cake SC by decreasing the number of stages of the nozzles, by decreasing the flow rate of hot water or steam sprayed from the nozzles, or by decreasing the number of stages of the nozzles and decreasing the flow rate of hot water or steam sprayed from the nozzles. The control means 26 then returns to Step ST51, to input a moisture content of the gypsum cake SC from the moisture measuring means H1.

Particularly, excessive moisture due to condensation of steam is prevented by maintaining the surface temperature of the gypsum cake SC to be equal to or lower than a predetermined value, thereby enabling to avoid a state of increasing moisture in the gypsum cake SC.

At Step ST52, when the input moisture content of the gypsum cake SC is not less than 10 wt % as the set value (NO at Step ST52), control returns to Step ST49. Furthermore, when the vacuum pressure has not increased more than the set value at Step ST46 (NO at Step ST46), when the salt concentration has not increased more than the set value at Step ST47 (NO at Step ST47), and when the specific resistance to filtration has not increased more than the set value at Step ST48 (NO at Step ST48), control proceeds to control according to the fourth embodiment described later.

As described above, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures a suction pressure by the vacuum suction mechanism 23, the impurity salt concentration measuring means C1 that measures a salt concentration as impurities in the absorber 1, the specific resistance-to-filtration measuring unit α that measures a specific resistance to filtration of the gypsum cake SC, the heating means 25 that heats the gypsum cake SC dewatered by the belt filter 22 by hot water or steam, the speed varying means (the drive unit 22c) that varies the belt advancing rate of the belt filter 22, and the control means 26 that controls a heated state by the heating means 25 and the belt advancing rate by the speed varying means, when the moisture content of the gypsum cake SC input from the moisture measuring means H1 has exceeded a predetermined amount, and an input value from at least one of the suction-pressure measuring means P1, the impurity salt concentration measuring means C1, and the specific resistance-to-filtration measuring unit α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1, the impurity salt concentration measuring means C1, and the specific resistance-to-filtration measuring means α.

In the control by the control means 26 described above, at Step ST42, when the input moisture content of the gypsum cake SC is equal to or more than 10 wt % as the set value (YES at Step ST42), the control means 26 inputs only the vacuum pressure of the belt filter 22 from the suction-pressure measuring means P1 (Step ST43), and may not perform input of the salt concentration in the absorber 1 from the impurity salt concentration measuring means C1 (Step ST44), and input of the specific resistance to filtration of the gypsum cake SC from the specific resistance-to-filtration measuring means α (Step ST45). That is, control is performed by the input of the vacuum pressure of the belt filter 22 from the suction-pressure measuring means P1.

That is, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures a suction pressure by the vacuum suction mechanism 23, the heating means 25 that heats the gypsum cake SC dewatered by the belt filter 22 by hot water or steam, the speed varying means (the drive unit 22c) that varies the belt advancing rate of the belt filter 22, and the control means 26 that controls the heated state by the heating means 25 and the belt advancing rate by the speed varying means, when the moisture content of the gypsum cake SC input from the moisture measuring means H1 has exceeded a predetermined amount, and an input value from the suction-pressure measuring means P1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the suction-pressure measuring means P1.

In the control by the control means 26 described above, at Step ST42, when the input moisture content of the gypsum cake SC is equal to or more than 10 wt % as the set value (YES at Step ST42), the control means 26 inputs only the salt concentration in the absorber 1 from the impurity salt concentration measuring means C1 (Step ST44), and may not perform input of the vacuum pressure of the belt filter 22 from the suction-pressure measuring means P1 (Step ST43), and input of the specific resistance to filtration of the gypsum cake SC from the specific resistance-to-filtration measuring means α (Step ST45). That is, control is performed by the input of the salt concentration in the absorber 1 from the impurity salt concentration measuring means C1.

As described above, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the impurity salt concentration measuring means C1 that measures a salt concentration as impurities in the absorber 1, the heating means 25 that heats the gypsum cake SC dewatered by the belt filter 22 by hot water or steam, the speed varying means (the drive unit 22c) that varies the belt advancing rate of the belt filter 22, and the control means 26 that controls the heated state by the heating means 25 and the belt advancing rate by the speed varying means, when the moisture content of the gypsum cake SC input from the moisture measuring means H1 has exceeded a predetermined amount, and an input value from the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the impurity salt concentration measuring means C1.

In the control by the control means 26 described above, at Step ST42, when the input moisture content of the gypsum cake SC is equal to or more than 10 wt % as the set value (YES at Step ST42), the control means 26 inputs only the specific resistance to filtration of the gypsum cake SC from the specific resistance-to-filtration measuring means α (Step ST45) and may not perform input of the vacuum pressure of the belt filter 22 from the suction-pressure measuring means P1 (Step ST43), and input of the salt concentration in the absorber 1 from the impurity salt concentration measuring means C1 (Step ST44). That is, control is performed by the input of the specific resistance to filtration of the gypsum cake SC from the specific resistance-to-filtration measuring means α.

As described above, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the specific resistance-to-filtration measuring means α that measures the specific resistance to filtration of the gypsum cake SC, the heating means 25 that heats the gypsum cake SC dewatered by the belt filter 22 by hot water or steam, the speed varying means (the drive unit 22c) that varies the belt advancing rate of the belt filter 22, and the control means 26 that controls the heated state by the heating means 25 and the belt advancing rate by the speed varying means, when the moisture content of the gypsum cake SC input from the moisture measuring means H1 has exceeded a predetermined amount, and an input value from the specific resistance-to-filtration measuring means α has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the specific resistance-to-filtration measuring means α.

In the control by the control means 26 described above, at Step ST42, when the input moisture content of the gypsum cake SC is equal to or more than 10 wt % as the set value (YES at Step ST42), the control means 26 inputs the vacuum pressure of the belt filter 22 from the suction-pressure measuring means P1 (Step ST43) and the salt concentration in the absorber 1 from the impurity salt concentration measuring means C1 (Step ST44), and may not perform input of the specific resistance to filtration of the gypsum cake SC from the specific resistance-to-filtration measuring means α (Step ST45). That is, control is performed by the input of the suction pressure of the belt filter 22 from the suction-pressure measuring means P1 and the input of the salt concentration in the absorber 1 from the impurity salt concentration measuring means C1.

As described above, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the suction-pressure measuring means P1 that measures the suction pressure by the vacuum suction mechanism 23, the impurity salt concentration measuring means C1 that measures a salt concentration as impurities in the absorber 1, the heating means 25 that heats the gypsum cake SC dewatered by the belt filter 22 by hot water or steam, the speed varying means (the drive unit 22c) that varies the belt advancing rate of the belt filter 22, and the control means 26 that controls the heated state by the heating means 25 and the belt advancing rate by the speed varying means, when the moisture content of the gypsum cake SC input from the moisture measuring means H1 has exceeded a predetermined amount, and an input value from at least one of the suction-pressure measuring means P1 and the impurity salt concentration measuring means C1 has deviated from a predetermined set value.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from at least one of the suction-pressure measuring means P1 and the impurity salt concentration measuring means C1.

In the control by the control means 26 described above, at Step ST42, when the input moisture content of the gypsum cake SC is equal to or more than 10 wt % as the set value (YES at Step ST42), the control means 26 can proceed to Step ST49 to perform control of the heated state by the heating means 25 and the belt advancing rate by the speed varying means. That is, control at Steps ST43 to ST48 may not be performed.

As described above, the gypsum dewatering device for a desulfurization facility according to the third embodiment is installed in the desulfurization facility 105 in which sulfur oxide in the flue gas G is absorbed by limestone in the absorbent A in the absorber 1, and includes the belt filter 22 that absorbs sulfur oxide and dewaters the gypsum slurry SS fed from the absorber 1 to form the gypsum cake SC, and the vacuum suction mechanism 23 that sucks moisture in the gypsum cake SC via the belt filter 22. The gypsum dewatering device also includes the moisture measuring means H1 that measures a moisture content of the gypsum cake SC to be dewatered by the belt filter 22, the heating means 25 that heats the gypsum cake SC dewatered by the belt filter 22 by hot water or steam, the speed varying means (the drive unit 22c) that varies the belt advancing rate of the belt filter 22, and the control means 26 that controls the heated state by the heating means 25 and the belt advancing rate by the speed varying means, when the moisture content of the gypsum cake SC input from the moisture measuring means H1 has exceeded a predetermined amount.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained.

Fourth Embodiment

Figure 8:
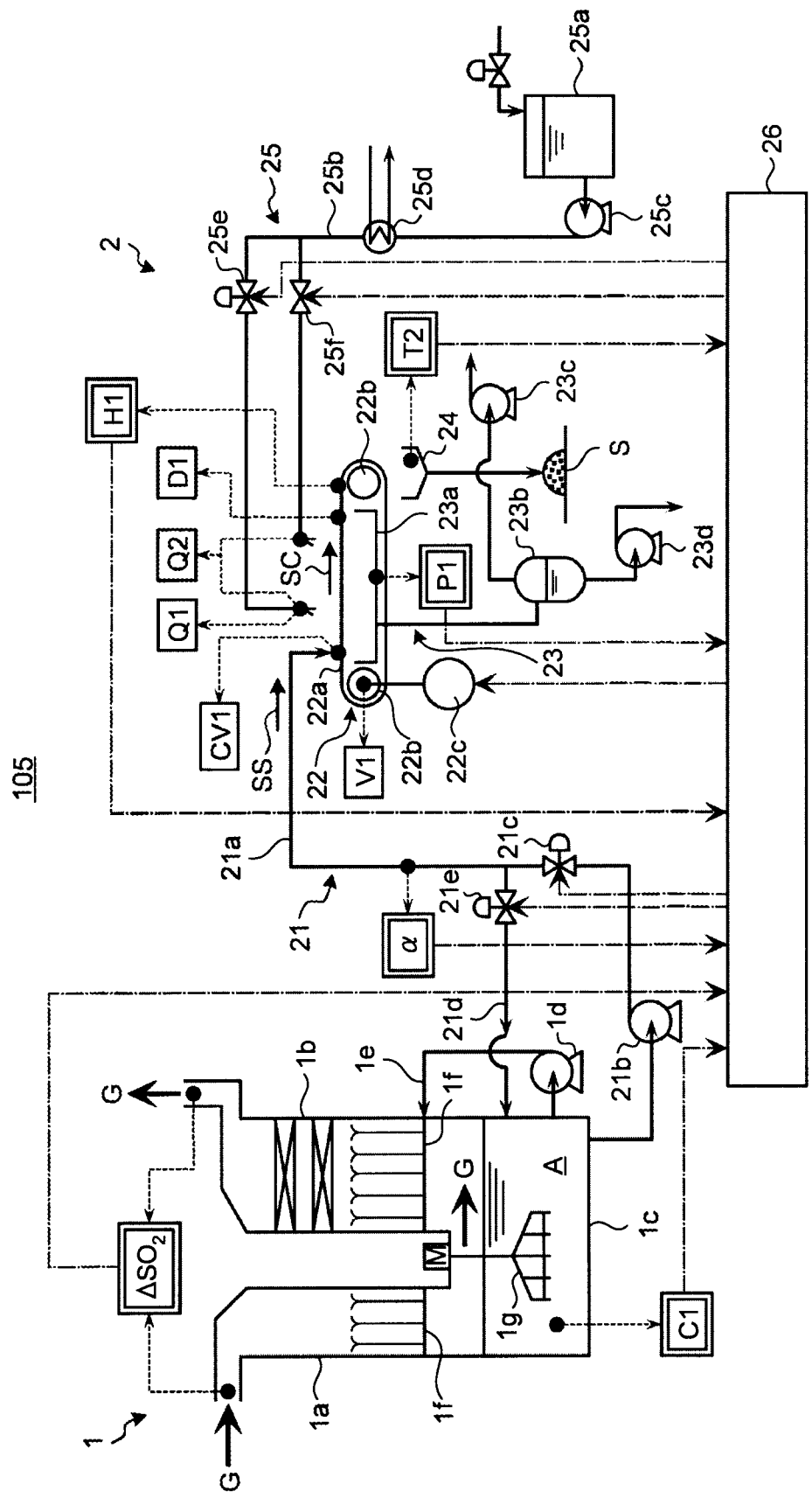
FIG. 8 is a schematic diagram of a gypsum dewatering device for a desulfurization facility according to a fourth embodiment of the present invention.

The fourth embodiment of the present invention is explained with reference to the drawings. FIG. 8 is a schematic diagram of a gypsum dewatering device for a desulfurization facility according to the present embodiment. In the fourth embodiment explained below, constituent elements equivalent to those of the first to third embodiments are denoted by like reference signs and explanations thereof will be omitted.

As shown in FIG. 8, the gypsum dewatering device 2 according to the present embodiment includes a desulfurization-amount measuring means $\Delta SO_2$ that measures an absorption amount of sulfur oxide in the absorber 1 in the first to third embodiments. The desulfurization-amount measuring means $\Delta SO_2$ calculates a desulfurization amount by measuring a gas concentration ($SO_2$ concentration) at an upper inlet of the inlet-side liquid-jet column 1a, which is an inlet of the flue gas G in the absorber 1 and at an upper outlet of the outlet-side liquid-jet column 1b, which is an outlet of the flue gas G in the absorber 1.

The gypsum dewatering device 2 according to the present embodiment also includes a transporting-rate varying means that varies a transporting rate of the gypsum cake SC to be dewatered by the belt filter 22 in the first, second, and third embodiments. The transporting-rate varying means is the extraction unit 21 described above, and specifically, is constituted of the valve 21c. That is, the transporting-rate varying means increases or decreases the flow rate of the gypsum slurry SS passing through the extraction pipe 21a by the valve 21c, to adjust the feed rate of the gypsum slurry SS to the belt filter 22 and adjust the transporting rate of the gypsum cake SC by the belt filter 22.

Measurement data of the moisture measuring means H1, the suction-pressure measuring means P1, the impurity salt concentration measuring means C1, the specific resistance-to-filtration measuring means $\alpha$, and the desulfurization-amount measuring means $\Delta SO_2$ are input to the control means 26. The control means 26 is a computer or the like. The control means 26 includes a RAM, a ROM and the like, and is provided with a storage unit (not shown) in which a program and data are stored. The data to be stored in the storage unit includes set values corresponding to values measured by the moisture measuring means H1, the suction-pressure measuring means P1, the impurity salt concentration measuring means C1, the specific resistance-to-filtration measuring means $\alpha$, and the desulfurization-amount measuring means $\Delta SO_2$. The set value of the moisture measuring means H1 is, for example, 10 wt %, and indicates a quality standard of the gypsum S. The set values of the suction-pressure measuring means P1, the impurity salt concentration measuring means C1, the specific resistance-to-filtration measuring means $\alpha$, and the desulfurization-amount measuring means $\Delta SO_2$ are set at the time of operating the gypsum dewatering device 2 to satisfy the quality standard of the gypsum S. The drive unit (the speed varying means) 22c of the belt filter 22 and the extraction unit (the transporting-rate varying means) 21 of the extraction unit 21 are connected to the control means 26. The control means 26 controls the drive unit 22c of the belt filter 22 and the valve 21c of the extraction unit 21 according to the program and data stored in the storage unit, based on the input values from the moisture measuring means H1, the suction-pressure measuring means P1, the impurity salt concentration measuring means C1, the specific resistance-to-filtration measuring means α, and the desulfurization-amount measuring means $\Delta SO_2$.

Control by the control means 26 is explained below with reference to a flowchart in FIG. 9.

The control starts when the respective input values of the suction-pressure measuring means P1, the impurity salt concentration measuring means C1, and the specific resistance-to-filtration measuring means α have not deviated from a predetermined set values, even when the moisture content of the gypsum cake SC input from the moisture measuring means H1 has exceeded a predetermined amount in the controls shown in FIGS. 3, 5, and 7. That is, when "NO" at Steps ST6, ST7, and ST8 in FIG. 3, "NO" at Steps ST26, ST27, and ST28 in FIG. 5, and "NO" at Steps ST46, ST47, and ST48 in FIG. 7.

Figure 9:
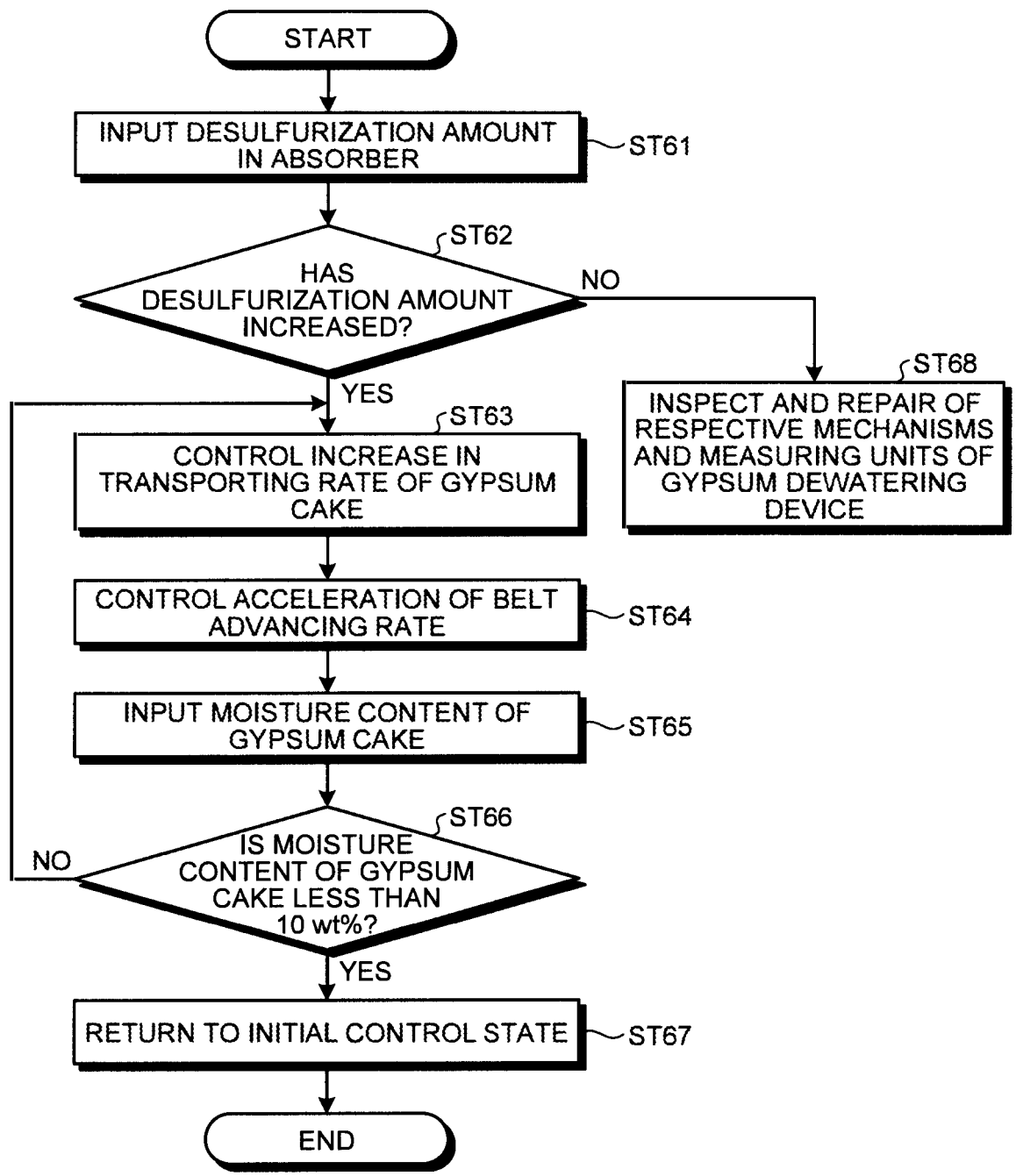
FIG. 9 is a flowchart of control by the gypsum dewatering device for a desulfurization facility according to the fourth embodiment of the present invention.

In this case, as shown in FIG. 9, the control means 26 inputs a desulfurization amount in the absorber 1 from the desulfurization-amount measuring means $\Delta SO_2$ (Step ST61). When the desulfurization amount has increased more than a predetermined amount (YES at Step ST62), the control means 26 controls an increase in the transporting rate by the transporting-rate varying means (Step ST63). That is, the control means 26 controls the valve 21c of the extraction unit 21 in an opening direction, and increases the feed rate of the gypsum slurry SS to be fed to the belt filter 22, thereby increasing the transporting rate of the gypsum cake SC to be dewatered by the belt filter 22. Furthermore, the control means 26 controls a belt advancing rate by the speed varying means (Step ST64). That is, the control means 26 accelerates the rotation speed of the rollers 22b by controlling the drive unit 22c of the belt filter 22 to accelerate the belt advancing rate (V1), thereby increasing the feed rate (CV1) of the gypsum cake SC while suppressing an increase in the thickness (D1) of the gypsum cake SC.

When the desulfurization amount has increased more than the predetermined amount, that is, because an increase in the formed gypsum slurry SS is expected, the transporting rate of the gypsum cake SC to be dewatered by the belt filter 22 is increased and the thickness (D1) of the gypsum cake SC is decreased so as not to decrease the specific resistance to filtration, thereby restoring the dewatering performance.

Next, the control means 26 inputs a moisture content of the gypsum cake SC from the moisture measuring means H1 (Step ST65). Next, when the input moisture content of the gypsum cake SC is less than 10 wt % as the set value (YES at Step ST66), the control means 26 returns the transporting-rate varying means and the speed varying means to initial control states (Step ST67), to finish the control.

At Step ST66, when the input moisture content of the gypsum cake SC is not less than 10 wt % as the set value (NO at Step ST66), control returns to Step ST63. Furthermore, when the desulfurization amount has not increased more than the set value at Step ST62 (NO at Step ST62), an operator is urged to perform inspection and repair of the respective devices and respective measuring means of the gypsum dewatering device 2 (Step ST68).

As described above, the gypsum dewatering device for a desulfurization facility according to the fourth embodiment includes, in the first to third embodiments described above, the control means 26 that controls an increase in the transporting rate by the transporting-rate varying means (the valve 21c) and the belt advancing rate by the speed varying means (the drive unit 22c), when the respective input values of the suction-pressure measuring means P1, the impurity salt concentration measuring means C1, and the specific resistance-to-filtration measuring means α have not deviated from a predetermined set value, even when the moisture content of the gypsum cake SC input from the moisture measuring means H1 has exceeded a predetermined amount, and when the absorption amount input from the desulfurization-amount measuring means $\Delta SO_2$ has exceeded a predetermined amount.

According to the gypsum dewatering device for a desulfurization facility, the moisture content of the dewatered gypsum cake SC in the belt filter 22 is measured and monitored at all times by using the moisture measuring means H1, thereby quickly ascertaining insufficient dewatering and promptly restoring the insufficient dewatering. Accordingly, the dewatering performance for dewatering the gypsum cake SC can be maintained. Furthermore, an initial indication of a decrease in the dewatering performance can be ascertained by the input value from the desulfurization-amount measuring means $\Delta SO_2$, even when it is difficult to ascertain an initial indication of a decrease in the dewatering performance by the input value from at least one of the suction-pressure measuring means P1, the impurity salt concentration measuring means C1, and the specific resistance-to-filtration measuring means α.

INDUSTRIAL APPLICABILITY

As described above, the gypsum dewatering device for a desulfurization facility according to the present invention is suitable for maintaining the dewatering performance.

REFERENCE SIGNS LIST 1 absorber
2 gypsum dewatering device
21 extraction unit
21c valve (transporting-rate varying means)
22 belt filter
22c drive unit (speed varying means)
23 vacuum suction mechanism
24 hopper
25 heating means
25e flow-rate adjusting valve
25f opening and closing valve
26 control means
105 desulfurization facility
G flue gas
A absorbent
SS gypsum slurry
SC gypsum cake
S gypsum
H1 moisture measuring means
P1 suction-pressure measuring means
C1 impurity salt concentration measuring means
α specific resistance-to-filtration measuring means
T2 surface-temperature measuring means
$\Delta SO_2$ desulfurization-amount measuring means

The invention claimed is:

1. A gypsum dewatering device for a desulfurization facility that is installed in a desulfurization facility in which sulfur oxide in flue gas is absorbed by limestone in an absorbent in an absorber, comprising:
a belt filter that absorbs the sulfur oxide and dewaters gypsum slurry fed from the absorber to form a gypsum cake;
a vacuum suction mechanism that sucks moisture in the gypsum cake via the belt filter;
a moisture measuring unit that measures a moisture content of the gypsum cake to be dewatered by the belt filter;
a heating unit that heats the gypsum cake to be dewatered by the belt filter by hot water or steam; and
a control unit that controls a heated state by the heating unit, when a moisture content of the gypsum cake input from the moisture measuring unit has exceeded a predetermined amount.

2. The gypsum dewatering device for a desulfurization facility according to claim 1, further comprising a suction-pressure measuring unit that measures a suction pressure by the vacuum suction mechanism, wherein
when the moisture content of the gypsum cake input from the moisture measuring unit has exceeded a predetermined amount and an input value from the suction-pressure measuring unit has deviated from a predetermined set value, the control unit controls a heated state by the heating unit.

3. The gypsum dewatering device for a desulfurization facility according to claim 1, further comprising an impurity salt concentration measuring unit that measures a salt concentration as impurities in the absorber, wherein
when the moisture content of the gypsum cake input from the moisture measuring unit has exceeded a predetermined amount and an input from the impurity salt concentration measuring unit has deviated from a predetermined set value, the control unit controls a heated state by the heating unit.

4. The gypsum dewatering device for a desulfurization facility according to claim 1, further comprising a specific resistance-to-filtration measuring unit that measures a specific resistance to filtration of the gypsum cake, wherein
when the moisture content of the gypsum cake input from the moisture measuring unit has exceeded a predetermined amount and an input value from the specific resistance-to-filtration measuring unit has deviated from a predetermined set value, the control unit controls a heated state by the heating unit.

5. The gypsum dewatering device for a desulfurization facility according to claim 1, further comprising:
a suction-pressure measuring unit that measures a suction pressure by the vacuum suction mechanism; and
an impurity salt concentration measuring unit that measures a salt concentration as impurities in the absorber, wherein
when the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls a heated state by the heating unit.

6. The gypsum dewatering device for a desulfurization facility according to claim 1, further comprising:
a suction-pressure measuring unit that measures a suction pressure by the vacuum suction mechanism;
an impurity salt concentration measuring unit that measures a salt concentration as impurities in the absorber; and
a specific resistance-to-filtration measuring unit that measures a specific resistance to filtration of the gypsum cake, wherein
when the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls a heated state by the heating unit.

7. The gypsum dewatering device for a desulfurization facility according to claim 1, further comprising a surface-temperature measuring unit that measures a surface temperature of the gypsum cake, wherein
when a surface temperature input from the surface-temperature measuring unit is not equal to or lower than a predetermined value, the control unit controls to decrease heating by the heating unit.

8. A gypsum dewatering device for a desulfurization facility that is installed in a desulfurization facility in which sulfur oxide in flue gas is absorbed by limestone in an absorbent in an absorber, comprising:
a belt filter that absorbs the sulfur oxide and dewaters gypsum slurry fed from the absorber to form a gypsum cake;
a vacuum suction mechanism that sucks moisture in the gypsum cake via the belt filter;
a moisture measuring unit that measures a moisture content of the gypsum cake to be dewatered by the belt filter;
a speed varying unit that varies a belt advancing rate by the belt filter; and
a control unit that controls a belt advancing rate by the speed varying unit, when a moisture content of the gypsum cake input from the moisture measuring unit has exceeded a predetermined amount.

9. The gypsum dewatering device for a desulfurization facility according to claim 8, further comprising a suction-pressure measuring unit that measures a suction pressure by the vacuum suction mechanism, wherein
when the moisture content of the gypsum cake input from the moisture measuring unit has exceeded a predetermined amount and an input value from the suction-pressure measuring unit has deviated from a predetermined set value, the control unit controls a belt advancing rate by the speed varying unit.

10. The gypsum dewatering device for a desulfurization facility according to claim 8, further comprising an impurity salt concentration measuring unit that measures a salt concentration as impurities in the absorber, wherein
when the moisture content of the gypsum cake input from the moisture measuring unit has exceeded a predetermined amount and an input value from the impurity salt concentration measuring unit has deviated from a predetermined set value, the control unit controls a belt advancing rate by the speed varying unit.

11. The gypsum dewatering device for a desulfurization facility according to claim 8, further comprising a specific resistance-to-filtration measuring unit that measures a specific resistance to filtration of the gypsum cake, wherein
when the moisture content of the gypsum cake input from the moisture measuring unit has exceeded a predetermined amount and an input value from the specific resistance-to-filtration measuring unit has deviated from a predetermined set value, the control unit controls a belt advancing rate by the speed varying unit.

12. The gypsum dewatering device for a desulfurization facility according to claim 8, further comprising:
a suction-pressure measuring unit that measures a suction pressure by the vacuum suction mechanism; and
an impurity salt concentration measuring unit that measures a salt concentration as impurities in the absorber, wherein
when the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls a belt advancing rate by the speed varying unit.

13. The gypsum dewatering device for a desulfurization facility according to claim 8, further comprising:
a suction-pressure measuring unit that measures a suction pressure by the vacuum suction mechanism;
an impurity salt concentration measuring unit that measures a salt concentration as impurities in the absorber; and
a specific resistance-to-filtration measuring unit that measures a specific resistance to filtration of the gypsum cake, wherein
when the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls a belt advancing rate by the speed varying unit.

14. A gypsum dewatering device for a desulfurization facility that is installed in a desulfurization facility in which sulfur oxide in flue gas is absorbed by limestone in an absorbent in an absorber, comprising:
a belt filter that absorbs the sulfur oxide and dewaters gypsum slurry fed from the absorber to form a gypsum cake;
a vacuum suction mechanism that sucks moisture in the gypsum cake via the belt filter;
a moisture measuring unit that measures a moisture content of the gypsum cake to be dewatered by the belt filter;
a heating unit that heats the gypsum cake to be dewatered by the belt filter by hot water or steam;
a speed varying unit that varies a belt advancing rate by the belt filter; and
a control unit that controls both a heated state by the heating unit and a belt advancing rate by the speed varying unit, when a moisture content of the gypsum cake input from the moisture measuring unit has exceeded a predetermined amount.

15. The gypsum dewatering device for a desulfurization facility according to claim 14, further comprising a suction-pressure measuring unit that measures a suction pressure by the vacuum suction mechanism, wherein
when the moisture content of the gypsum cake input from the moisture measuring unit has exceeded a predetermined amount and an input value from the suction-pressure measuring unit has deviated from a predetermined set value, the control unit controls both a heated state by the heating unit and a belt advancing rate by the speed varying unit.

16. The gypsum dewatering device for a desulfurization facility according to claim 14, further comprising an impurity salt concentration measuring unit that measures a salt concentration as impurities in the absorber, wherein
when the moisture content of the gypsum cake input from the moisture measuring unit has exceeded a predetermined amount and an input value from the impurity salt concentration measuring unit has deviated from a predetermined set value, the control unit controls both a heated state by the heating unit and a belt advancing rate by the speed varying unit.

17. The gypsum dewatering device for a desulfurization facility according to claim 14, further comprising a specific resistance-to-filtration measuring unit that measures a specific resistance to filtration of the gypsum cake, wherein
when the moisture content of the gypsum cake input from the moisture measuring unit has exceeded a predetermined amount and an input value from the specific resistance-to-filtration measuring unit has deviated from a predetermined set value, the control unit controls both a heated state by the heating unit and a belt advancing rate by the speed varying unit.

18. The gypsum dewatering device for a desulfurization facility according to claim 14, further comprising:
a suction-pressure measuring unit that measures a suction pressure by the vacuum suction mechanism; and
an impurity salt concentration measuring unit that measures a salt concentration as impurities in the absorber, wherein
when the moisture content of the gypsum cake input from the moisture measuring unit has exceeded a predetermined amount and an input value from at least one of the suction-pressure measuring unit and the impurity salt concentration measuring unit has deviated from a predetermined set value, the control unit controls both a heated state by the heating unit and a belt advancing rate by the speed varying unit.

19. The gypsum dewatering device for a desulfurization facility according to claim 14, further comprising:
a suction-pressure measuring unit that measures a suction pressure by the vacuum suction mechanism;
an impurity salt concentration measuring unit that measures a salt concentration as impurities in the absorber; and;
a specific resistance-to-filtration measuring unit that measures a specific resistance to filtration of the gypsum cake, wherein
when the moisture content of the gypsum cake input from the moisture measuring unit has exceeded a predetermined amount and an input value from at least one of the suction-pressure measuring unit, the impurity salt concentration measuring unit, and the specific resistance-to-filtration measuring unit has deviated from a predetermined set value, the control unit controls both a heated state by the heating unit and a belt advancing rate by the speed varying unit.

20. The gypsum dewatering device for a desulfurization facility according to claim 14, further comprising a surface-temperature measuring unit that measures a surface temperature of the gypsum cake, wherein
when a surface temperature input from the surface-temperature measuring unit is not equal to or lower than a predetermined value, the control unit controls to decrease heating by the heating unit.

21. The gypsum dewatering device for a desulfurization facility according to claim 6, further comprising:
a desulfurization-amount measuring unit that measures an absorption amount of the sulfur oxide in the absorber;

a transporting-rate varying unit that varies a transporting rate of the gypsum cake to be dewatered by the belt filter; and a speed varying unit that varies a belt advancing rate of the belt filter, wherein when a moisture content of the gypsum cake input from the moisture measuring unit has exceeded a predetermined amount, if each input value of the suction-pressure measuring unit, the impurity salt concentration measuring unit, and the specific resistance-to-filtration measuring unit does not deviate from a predetermined set value, the control unit controls both an increase in the transporting rate of the transporting-rate varying unit and the belt advancing rate of the speed varying unit, when the absorption amount input from the desulfurization-amount measuring unit has exceeded a predetermined amount.

* * * * *